United States Patent [19]

Mullane, Jr.

[11] 4,184,175
[45] Jan. 15, 1980

[54] METHOD OF AND APPARATUS FOR OPTICALLY DETECTING ANOMALOUS SUBSURFACE STRUCTURE IN TRANSLUCENT ARTICLES

[75] Inventor: William I. Mullane, Jr., Cincinnati, Ohio

[73] Assignee: The Procter & Gamble Company, Cincinnati, Ohio

[21] Appl. No.: 767,008

[22] Filed: Feb. 9, 1977

[51] Int. Cl.² ............................................. H04N 7/18
[52] U.S. Cl. ...................... 358/93; 250/562; 250/563; 356/237; 358/106
[58] Field of Search ...................... 250/562, 563, 572; 356/237, 118, 119, 120, 204; 358/93, 106, 98

[56] References Cited

U.S. PATENT DOCUMENTS

| | | | |
|---|---|---|---|
| 3,176,306 | 3/1965 | Burns | 356/237 |
| 3,417,745 | 12/1968 | Sheldon | 350/96.26 |
| 3,439,988 | 4/1969 | Breske | 356/237 |
| 3,474,254 | 10/1969 | Piepenbrint et al. | 250/562 |
| 3,533,684 | 10/1970 | Stark et al. | 358/107 |
| 3,600,094 | 8/1971 | Liskowitz | 356/118 |
| 3,976,384 | 8/1976 | Matthews et al. | 250/563 |
| 3,986,777 | 10/1976 | Roll | 356/188 |

OTHER PUBLICATIONS

TV System Monitors Dental Surgery—Electronics—vol. 33—p. 92, Jan. 1, 1960.

Primary Examiner—Robert L. Griffin
Assistant Examiner—Joseph A. Orsino, Jr.
Attorney, Agent, or Firm—Thomas J. Slone; John V. Gorman; Richard C. Witte

[57] ABSTRACT

A nondestructive method of and apparatus for optically detecting the presence of and inferentially determining the relative degree of anomalous subsurface structure in translucent articles: for instance, such anomalous subsurface structural phenomena as pre-carious lesions in in vivo teeth. Moreover, dynamic changes in the degree of such anomalous subsurface structure can be identified and relatively quantified. Thus, for instance, progressive subsurface deterioration of teeth can be monitored, and the efficacy of products directed towards arresting or reversing the development of pre-carious lesions in teeth can be evaluated through the use of the present invention. The method and apparatus of the present invention provide for illuminating a surface area of a translucent article with incident light, and detecting whether a sufficient portion of the light is internally diverted by being refracted or diffusely reflected or the like by the internal structure of the article to indicate whether the subsurface structure of the article is anomalous. Both in vivo and in vitro apparatuses are disclosed. Several species of hand-held probes for such applications as dental examinations are also disclosed. Manipulation of the hand-held probes is facilitated by flexible fiber optic cables. The apparatus may include closed circuit video and automatic data processing equipment to facilitate the use of the apparatus, and to facilitate the reduction and interpretation of the data derived from operating the apparatus. As used herein, the term light is not intended to be limited to the visible spectrum.

31 Claims, 33 Drawing Figures

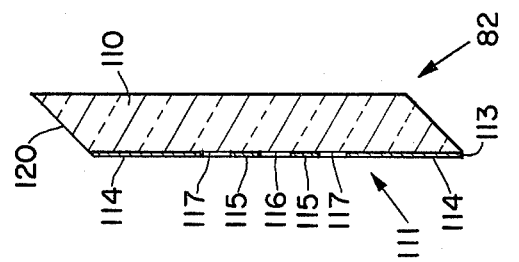
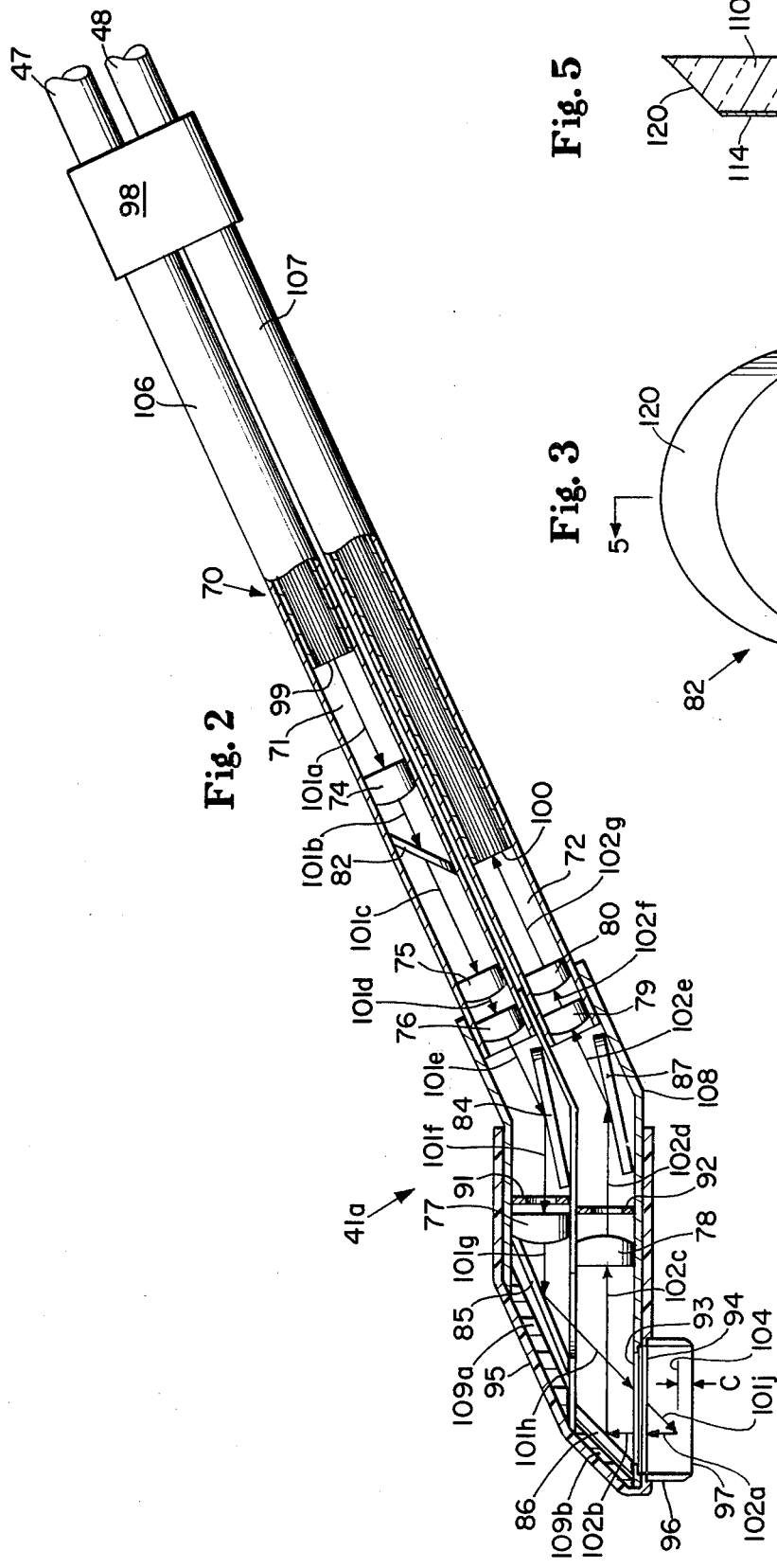
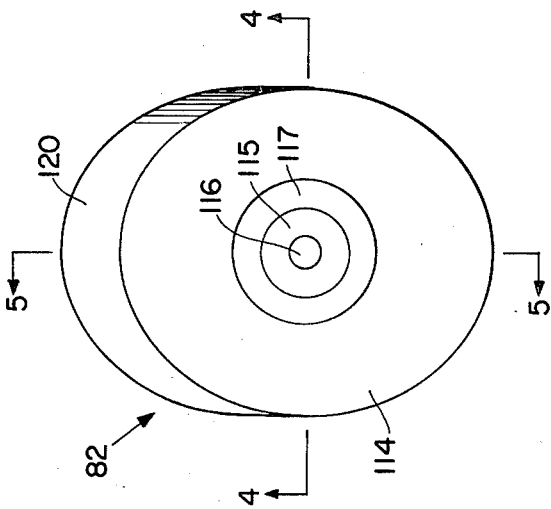
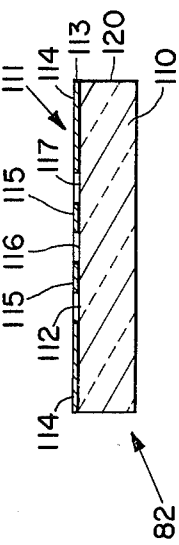

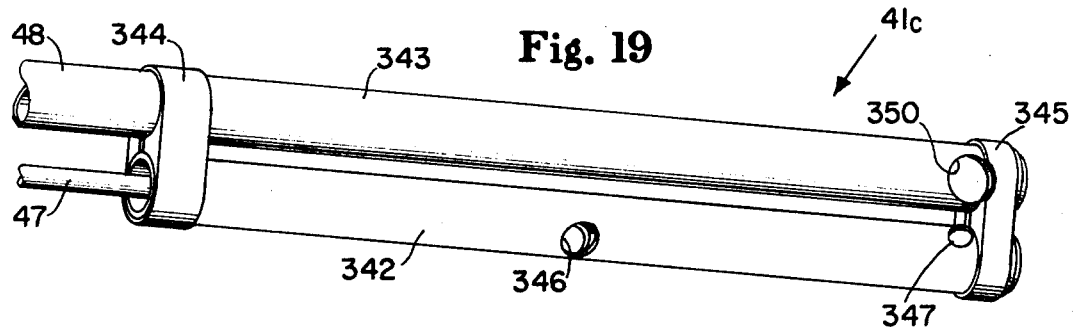
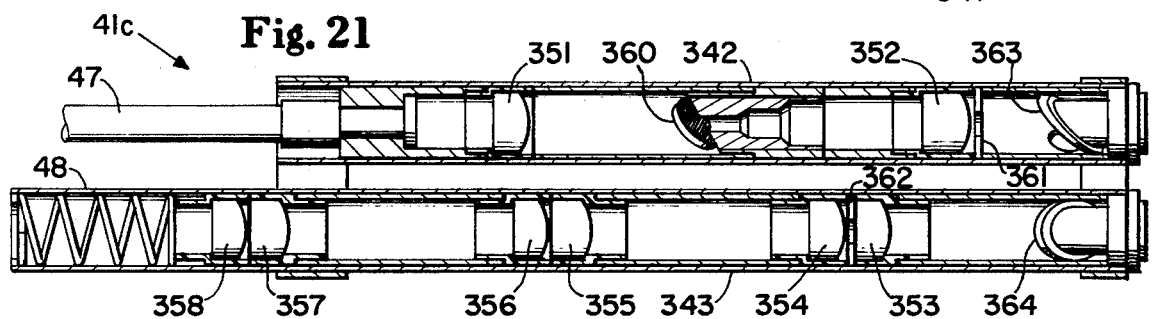
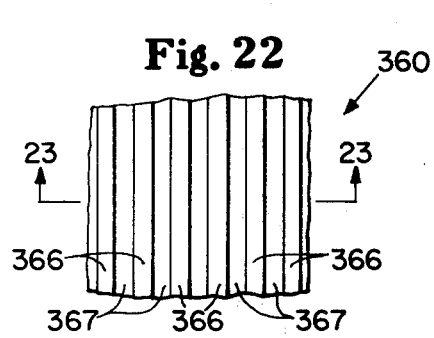
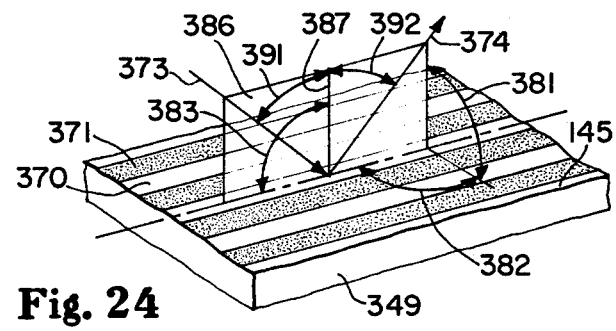
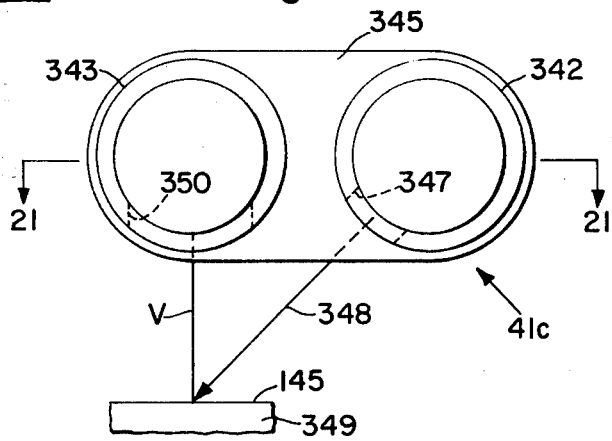

METHOD OF AND APPARATUS FOR OPTICALLY DETECTING ANOMALOUS SUBSURFACE STRUCTURE IN TRANSLUCENT ARTICLES

FIELD OF THE INVENTION

This invention generally relates to optically inspecting translucent articles for the purpose of discovering and relatively quantifying subsurface anomalous structure: for instance, minute defects or zones of voids (e.g., pre-carious lesions) in translucent crystaline articles such as teeth of human beings. Alternatively, subsurface anomalous structure could also include, for instance, but not be limited to nonporous or voidless zones of normally porous structures or structures normally having subsurface voids respectively; or structures having abnormal ranges of pore or void sizes, shapes, dispositions, orientations, and the like; or structures comprising inclusions of undesirable materials; or structures comprising abnormal quantities, sizes, or distributions of desirable inclusions, and the like.

While some subsurface anomalous structural defects in translucent articles result in visible surface manifestations (e.g., white spots on teeth), the present invention provides sufficient sensitivity and resolution for optically discovering and relatively quantifying subsurface defects which are not visually apparent to a naked eye.

BACKGROUND OF THE INVENTION

The prior art discloses methods of and apparatus for optically discovering surface phenomena such as roughness, flatness, distortion, and parallelism of front and back surfaces through the use of diffuse and/or specular surface reflections. See for instance: U.S. Pat. No. 2,446,628—Flatness Testing Apparatus which issued Aug. 10, 1948 to F. M. Brown; U.S. Pat. No. 3,430,055—Surface Flaw Detector which issued Feb. 25, 1969 to E. E. Metzger; U.S. Pat. No. 3,584,963—Optical Flaw Detector which issued June 15, 1971 to Daniel A. Wisner; U.S. Pat. No. 3,591,291—Method And Apparatus For Sensing Reflected Light And Diffused Light From A Surface To Indicate The Roughness Of Said Surface which issued July 6, 1971 to Milton Greer; U.S. Pat. No. 3,799,679—Glass Distortion Scanning System which issued Mar. 26, 1974 to Gabriel Simko; U.S. Pat. No. 3,804,521—Optical Device For Measuring Surface Roughness which issued April 16, 1974 to Robert A. Sprague; U.S. Pat. No. 3,857,637—Surface Distortion Analyzer which issued Dec. 31, 1974 to Robert J. Obenreder; and, U.S. Pat. No. 3,922,093—Device For Measuring The Roughness Of A Surface which issued Nov. 25, 1975 to Rene Dandliker et al. Also see U.S. Pat. No. 3,439,988—Apparatus For Inspecting A Reflective Surface Which Includes A Projector Of A Pattern Of Lines Having Different Thicknesses which issued Apr. 22, 1969 to C. D. Breske which causes the pattern of lines to be projected onto the reflective surface of interest and which enables discovering imperfections in the reflective surface of interest by looking for distortions in the reflected pattern lines on a screen. Document reading or scanning devices are also shown in the prior art. See for instance: U.S. Pat. No. 3,345,908—Print Characteristics Displayer which issued Oct. 10, 1967 to R. A. Jensen; and U.S. Pat. No. 3,792,268—Document Scanner Having Optical Diffusion Means which issued Feb. 12, 1974 to Brian Kenneth Bjerke et al. The prior art also discloses an optical comparitor having a coaxial fiber optic tip; reference U.S. Pat. No. 3,784,309 which issued Jan. 8, 1974 to Rene Brelot et al. However, the prior art does not disclose method or apparatus solutions to all of the problems associated with discovering and relatively quantifying subsurface anamolous structure in translucent articles in the manner of or to the degree of the present invention.

OBJECTS OF THE INVENTION

The nature and substance of the present invention will be more readily appreciated after giving consideration to its major aims and purposes. The principal objects of the invention are recited in the ensuing paragraphs in order to provide a better appreciation of its important aspects prior to describing the details of several embodiments in later portions of this description.

A principal object of the present invention is to provide an optical instrument or apparatus for discovering anomalous subsurface structure in translucent articles.

Another object of the present invention is to provide an optical instrument for discovering and relatively quantifying anomalous subsurface structure in translucent articles.

Yet another object of the present invention is providing an optical instrument for discovering and relatively quantifying subsurface structural defects in translucent articles substantially regardless of the condition of the surface; e.g., rough or smooth.

Still yet another object of the present invention is providing an optical instrument comprising a hand-held probe such as a dental probe for in vivo discovery and relative quantification of subsurface anomalous structural defects in translucent articles such as human teeth.

Yet still another object of the present invention is providing the optical instruments and apparatus described in the preceding paragraphs which further provide for drying a translucent article so that wetness of the article does not interfere with examining the article for the purpose of discovering anomalous subsurface structure.

A still further object of the present invention is providing the optical instruments and apparatus described in the preceding paragraphs which further provide substantial immunity from ambient light.

Another still further object of the present invention is providing a method of discovering and quantifying anomalous subsurface structure or defects in translucent articles such as in vivo human teeth which method includes detecting and quantifying light which has been diverted by internal structure of the articles, and may include obviating ambient light from interfering with such discovering and quantifying.

SUMMARY OF THE INVENTION

These and other objects of the present invention are achieved by providing a method of and apparatus for optically discovering subsurface anomalous structure in a translucent article by illuminating a surface area of the article with incident light, and by detecting whether a sufficient portion of the incident light is diverted as by diffuse reflection or refraction or the like by internal structure of the article to indicate or permit the inference of the presence of subsurface anomalous structure in the article. The apparatus may include means for imposing a predetermined pattern on a beam of incident light on a surface area of a translucent article, means for detecting light which has been diverted from its incident path by the article, and means for obviating diffuse and specular surface reflection from the surface area from being received by the means provided for detecting light which has been diverted from its incident path by the article whereby the means for detecting diverted light is made responsive only to light which has been diverted by subsurface structure of the article. The invention may further include a closed circuit video system, an automatic data system, a hand-held optical probe, spacing means for facilitating correctly spacing the probe from the article being examined, means for drying the article being examined, and means for obviating ambient light.

BRIEF DESCRIPTION OF THE DRAWINGS

While the specification concludes with claims particularly pointing out and distinctly claiming the subject matter regarded as the present invention, it is believed the invention will be better understood from the following description taken in connection with the accompanying drawings in which:

FIG. 2 is a side elevational sectional view of a preferred embodiment optical probe constructed in accordance with the present invention.

FIG. 3 is a plan view of a reticle which is incorporated in the optical probe shown in FIG. 2.

FIGS. 4 and 5 are sectional views of the reticle shown in FIG. 3 which views are taken along lines 4—4, and 5—5 respectively of FIG. 3.

FIG. 19 is a fragmentary perspective view of an alternate embodiment hand-held optical probe constructed in accordance with the present invention.

FIG. 20 is an end view of the optical probe shown in FIG. 19.

FIG. 21 is a sectional view taken along line 21—21 of FIG. 20 but in which view the optical members of the probe have not been sectioned.

FIG. 22 is an enlarged scale, fragmentary view of the reticle of the optical probe shown in FIG. 21.

FIG. 23 is a fragmentary sectional view taken along line 23—23 of FIG. 22.

FIG. 24 is a greatly enlarged scale, perspective view of a fragmentary portion of an article having a portion of its surface area illuminated by a patterned incident light beam issuing from the optical probe shown in FIGS. 19 through 21 inclusive.

DESCRIPTION OF THE PREFERRED EMBODIMENT

Figure 1:
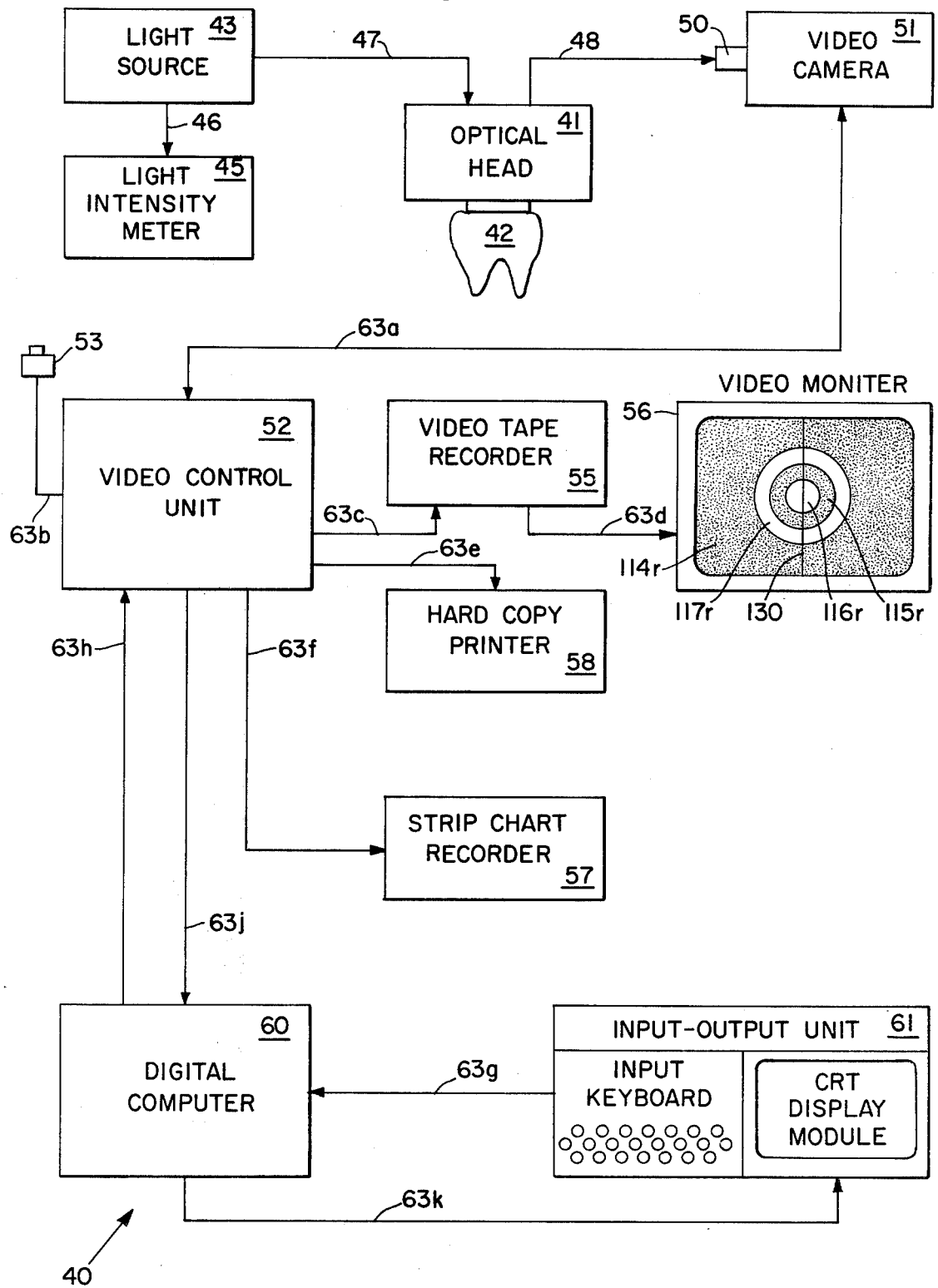
FIG. 1 is a block diagram of an optical instrumentation system embodying the present invention.

With continuing reference to the accompanying drawings in which drawings the same designators are used to identify identical parts and features, FIG. 1 shows a block diagram of a preferred optical instrumentation system 40 embodying the present invention. The optical instrumentation system 40 is alternately designated herein as apparatus 40.

The optical instrumentation system 40 comprises an optical head 41 for examining a translucent article such as a tooth 42, a light source 43, a light intensity meter 45, two incoherent fiber optic cables 46 and 47, a coherent fiber optic cable 48, a video relay lens 50, a video camera 51, a video control unit 52, a scan initiate switch 53, a video tape recorder 55, a video monitor 56, a strip chart recorder 57, a hard copy printer 58, a digital computer 60, an input-output unit 61, and cables 63a through 63h, 63j, and 63k.

Briefly, the optical instrumentation system 40, FIG. 1, provides means for illuminating a surface area of a translucent article such as a tooth with incident light through optical head 41, and means including a closed circuit video system and a computer system for detecting whether a sufficient portion of the incident light is diffusely reflected or otherwise internally diverted by subsurface structure of the article to indicate the presence of anomalous subsurface structure in the article. As used herein, the term light is not intended to be limited to the visible spectrum.

Figure 7:
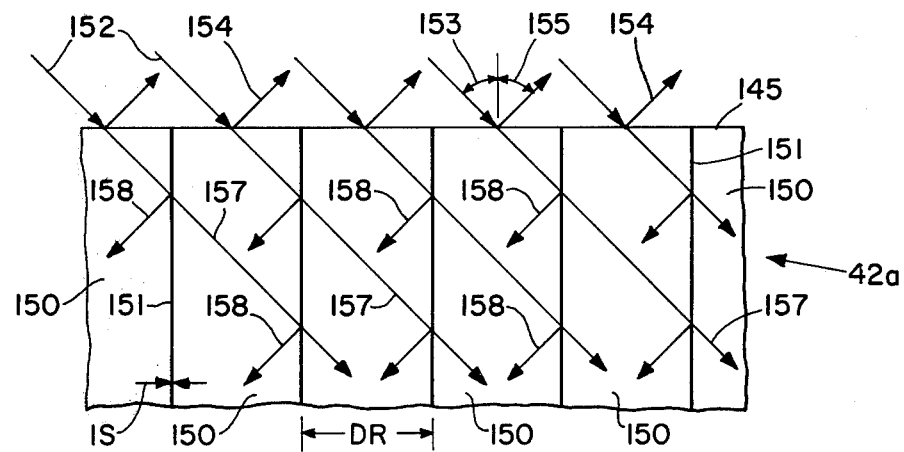
FIGS. 7 and 8 are fragmentary, greatly enlarged scale sectional views of somewhat schematic representations of a normal sound tooth, and a tooth having a pre-carious lesion, respectively.

By way of background, a sound tooth is a translucent crystalline structure which precipitates only a relatively minor level of outwardly directed, internally diverted light from immediately subjacent an illuminated portion of its surface when that portion is illuminated by inwardly directed oblique incident light. It is believed this results because, as indicated in FIG. 7 which is described hereinafter, the incident light propagates deeply in a sound tooth for want of reflective and refractive interfaces and the like which would internally divert some of the light upwardly/outwardly from internal the illuminated, translucent tooth. When similarly illuminated, an unsound tooth having subsurface defects such as zones of very tiny voids (which zones are alternatively termed pre-carious lesions) will precipitate a substantial amount of upwardly/outwardly directed internally diverted light such as the subsurface diffusely reflected light indicated in FIG. 8 which is also described hereinafter.

It has been discovered that the relative intensity or level of such internally diverted light correlates with the relative degree of anomalous subsurface structure in a translucent article. Therefore, the optical instrumentation system 40 can be empirically calibrated as indicated by the graph, FIG. 13, as described hereinafter. Furthermore, the optical instrumentation system 40 provides high sensitivity, magnification and resolution so that, for instance, such dental defects as pre-carious lesions can be discovered and treated at an early stage: i.e., before becoming large enough to be visible to a naked eye, or before a cavity is formed, or without having to subject dental patients to conventional radiographic examinations.

While the foregoing brief description of optical system 40, and the following descriptions place the present invention in a dental application context, it is not intended to thereby limit the scope of the present invention to dental applications.

The optical head 41, FIG. 1, may be a hand-held optical probe such as shown in FIG. 2 and designated probe 41a. Probe 41a comprises a body 70 having an incident light passageway 71 and a diverted or return or viewing light passageway 72, lenses 74 through 80, a reticle 82, front surface mirrors 84 through 87, aperture discs 91 and 92, a circularly-polarizing filter 93, a transparent window 94, a cover 95, a resilient tubular member 96 having a distal end 97, and a coupling 98 for receiving ends 99 and 100 of fiber optic cables 47 and 48, respectively, so that the ends 99 and 100 extend into passageways 71, 72, respectively. The path for incident light is indicated by arrows 101a through 101h and 101j, and the path for return light is indicated by arrows 102a through 102g. The focal planes of both the projection optics and the return light optics are coincident and are designated singularly hereinafter as focal plane 104. Focal plane 104 extends parallel to the distal end 97 of member 96 and is spaced towards window 94 a distance designated C from end 97. As indicated by arrow 101h, the path of the incident light is oblique with respect to focal plane 104 and, as indicated by arrow 102a, the path of the return light is normal to focal plane 104.

The probe 41a, FIG. 2, comprises means for receiving light from a remote light source 43, FIG. 1, via fiber optic cable 47, means for converting the received light into an image carrying incident light beam, and means for projecting the image carrying incident light beam through the transparent window 94 and for focusing the image carried by the beam in focal plane 104. The angle of incidence of the incident beam with respect to focal plane 104 in the preferred embodiment probe 41a is nominally forty-five (45) degrees. The probe 41a further comprises means for receiving light returning from the illuminated region of focal plane 104 through window 94, and causing such returning light to be transmitted to and focused on the end 100 of the image carrying coherent fiber optic cable 48.

The members of probe 41a, FIG. 2, are so configured and disposed that: when a surface of interest of an article to be examined through the use of probe 41a is placed in focal plane 104, a two power enlarged image of an image pattern on reticle 82 is projected onto the surface of interest; and a half power reduced-size image of the projected image is focused on end 100 of fiber optic cable 48. Moreover, the members of the probe 41a are so configured that the line-of-sight of the viewing portion (return light portion) of probe 41a is opposite to arrow 102a which is substantially normal to the focal plane 104, and the angle of acceptance of the return light optics is such that any portion of the incident light beam which is specularly reflected from flat or slightly concave or convex surfaces of interest disposed in the depths of field of both the image projection optics and the return light optics is substantially precluded from reaching the end 100 of the coherent fiber optic cable 48. Thus, the closed circuit video will view the illuminated surface of interest along a line-of-sight which is opposite to arrow 102a which is normal to focal plane 104.

The purpose of the circularly-polarizing filter 93, FIG. 2, is to further obviate transmission to the video system of any of the incident light which is diffusely or specularly reflected from the illuminated surface of interest.

Body 70 of probe 41a, FIG. 2, comprises two stainless steel tubular members 106 and 107, a nosepiece 108, plugs 109a and 109b, and the coupling 98 which are rigidly secured together in the relation shown in FIG. 2. That is, one end of each tubular member 106, 107 is inserted into a suitably sized hole provided in the nosepiece 108 while the other ends of the tubular members are secured in suitably sized holes provided in coupling 98. Thus, the tubular members 106 and 107 are disposed in over-and-under parallel relation. The tubular members 106 and 107 of an exemplary probe 41a have outer diameters of one-quarter inch and have internal diameters of about two-hundred-and-thirty-thousandths of an inch. The nosepiece 108 has a twenty-five degree offset which offset has been determined to be useful for enabling dental examinations.

In the preferred embodiment probe 41a, lens 74 is an anti-reflection coated aspheric lens having a focal length of twelve millimeters, lenses 75 through 80 are anti-reflection coated plano-convex achromatic lenses having thirty millimeter focal lengths, aperture discs 91 and 92 have three millimeter diameter apertures through them, incoherent fiber optic cable 47 comprises a fiber bundle having an active diameter of five-thirty seconds of an inch, and the coherent fiber optic cable 48 is a Custom Fiberscope imaging cable having a bundle of ten micron diameter fibers which bundle has an active diameter of three-and-one-half millimeters. Such a cable is available from the American Optical Corporation, Fiber Optics Division, Southbridge, Mass., Zip Code 01550.

Reticle 82, FIGS. 3 through 5, comprises an oval-shape transparent blank 110 having an image pattern 111 formed on one planar surface 112 which pattern comprises a border 114 and a ring 115 of opaque material 113. The relative thickness of the opaque material 113 is greatly exaggerated in FIGS. 4 and 5 in order to clearly show its presence. Thus, light can be transmitted through a centrally disposed circular area 116, and an annular area 117 of the reticle 82. The edge 120 of the reticle 82 appears normal to surface 112 in FIG. 4 and beveled at forty-five (45) degrees in FIG. 5 because the reticle 82 is inclined at an angle of forty-five (45) degrees in passageway 71, FIG. 2. By inclining the reticle 82 with respect to the center line of passageway 71 at an angle equal to the angle of incidence of the projected beam with respect to the focal plane 104, the array of circles of the image pattern 111 are also circles in the projected image. That is, the projected image in focal plane 104 is a true image of the image pattern 111 rather than being eliptically distorted. In the preferred embodiment probe 41a, the image pattern 111 was formed by nickel plating the entire surface 112 of a glass blank 110; and by then etching the plating away in the circular area 116 and the annular area 117. The diameter of the circular area 116 in reticle 82 of the preferred embodiment probe 41a is twenty-thousandths of an inch, and the inside and outside diameters of annular area 117 are sixty-thousandths and one-hundred-thousandths of an inch, respectively.

Referring back to FIG. 2, the resilient tubular member 96 extends a distance C beyond focal plane 104. This provides means for obviating ambient light from the surface of interest on an article being examined through the use of probe 41a because, being resilient, member 96 will conform to the surface of interest when the probe 41a is pressed against the surface of interest with sufficient force to cause the focal plane 104 to be substantially coextensive with the surface of interest. Conversely, the resilient tubular member 96 comprises means for requiring that the probe 41a be pressed against the surface of interest with sufficient force to cause the focal plane 104 to become nominally coextensive with the surface of interest even through the surface of interest may in fact be somewhat concave or convex. By requiring such pressing, the probe can be hand-held more steadily by a user than if such pressing were not required.

The resilient tubular member 96 is secured to the cover 95 so that they can be replaced as a sterile unit as would be desirable, for instance, for each dental patient. Alternatively, cover 95 and member 96 could be integrated into a unitary structure, not shown in the figures.

The light source 43, FIG. 1, of the preferred system 40 may be, for instance, a Model 8 which is available from the Skia Corp., Campbell, Calif.

The light intensity meter 45 is provided to monitor the output intensity of light source 43 so that the user can adjust the light source 43 as required to maintain a relatively constant output light intensity via cable 47 to the optical head 41.

The video relay lens 50 of system 40, FIG. 1, is a one power relay lens.

The video camera 51 of system 40, FIG. 1, may be a Model No. 502 available from Colorado Video Inc., Boulder, Colo., 80302.

The video control unit 52 of system 40, FIG. 1, may comprise a Video Analyzer Model 321, a Synchronizing Generator Model 601B, and a Camera Module 502 which are all available from Colorado Video Inc., Boulder, Colo., 80302.

The scan switch 53 of system 40, FIG. 1, may be a Clipper Switch, Cat. No. 635-S which is available from Linemaster Switch Corp., Woodstock, Conn.

The video tape recorder 55, FIG. 1, may be a Panasonic Model NV-8030 and the video monitor 56 may be a Panasonic Model TR-920M which are both available from Matsushita Electric Industrial Co. Ltd., Japan.

The strip chart recorder 57, FIG. 1, may be a Mark 280 Brush Recorder, Model 15-6327-10 which is available from the Brush Instruments Division of Gould Inc., 3631 Perkins Avenue, Cleveland, Ohio, 44114.

The hard copy printer 58, FIG. 1, may be a Video Hard Copy Unit such as a Tektronic Model 4632 which is available from the Information Display Division, Tektronic, Inc., P.O. Box 500, Beaverton, Oreg., 97077. The printer 58 provides means for storing picture-type information (that which is displayed on the video monitor 56) in a picture-type format which, it is believed, will be very useful for maintaining dental patient records.

The digital computer 60, FIG. 1, may be a PDP-11, and the input-output unit 61 may be a Model VT 52AE which are both available from the Digital Equipment Corp., Maynard, Mass., 01754.

The cables 63a through 63h, 63j and 63k, FIG. 1, provide electrical interconnection means to enable the system 40 to operate as hereinafter described.

The operation of system 40, FIG. 1, will be described as comprising probe 41a which has been described in detail rather than optical head 41 per se.

In the operation of system 40, FIG. 1, light is conducted by the incoherent fiber optic cable 47 from the light source 43 to the optical probe 41a, FIG. 2. In probe 41a, as described hereinbefore, the light received via fiber optic cable 47 is formed into a beam and has an image impressed on it by passing it through reticle 82. The image carrying beam is then, as indicated by arrow 101j, obliquely projected to and focused in focal plane 104. The probe 41a is then positioned with respect to a surface of interest of a translucent article such as tooth 42, FIG. 1, which article is to be examined for subsurface anomalous structure so that the surface of interest is nominally coextensive with focal plane 104 or is in the depths of field of both the image projection optics and the return light optics.

The video camera 51 is then operated through the video control unit 52 in a manner well known by persons of ordinary skill in the art of closed circuit video so that the video camera views the illuminated surface of interest along a light-of-sight substantially normal to the surface of interest and sees the area thereof which is illuminated by the incident light beam. What the video camera views is then forwarded from the video control unit 52 via cable 63c to the video tape recorder 55 in which it can be recorded for later playback, or through which it can be forwarded via cable 63d to and displayed on the face of the video monitor 56.

As shown in FIG. 1, the picture on the video monitor is a greatly enlarged image of the image pattern of concentric rings on reticle 82 described hereinbefore. Therefore, to conveniently correlate the designators used with respect to reticle 82, FIGS. 3–5, the centrally disposed light circle on the video monitor is designated 116r, the annular-shape shadow ring is designated 115r, the annular-shape light ring is designated 117r, and the shadow area surrounding light ring 117r is designated 114r.

As explained hereinbefore, the light received by the video camera 51 must be the portion of the incident light beam which has been diffusely reflected or otherwise internally diverted by subsurface structure of tooth 42. That is, because the resilient member 96 obviates ambient light, and because the angle of acceptance of the return light optics substantially obviates therefrom light which has been specularly reflected from the illuminated surface of the tooth, and because the circularly-polarizing filter 93 substantially obviates the transmission of diffuse and specular surface reflected light to the video system, the light which is transmitted to the video system must be that which has been diffusely reflected or otherwise internally diverted by the structure of the tooth subjacent the illuminated surface area. Therefore, a high degree of contrast between the lighted areas 116r and 117r, and the shaded areas 114r and 115r, indicates a high degree of light diverting structure in the tooth 42 subjacent the illuminated surface. Conversely, a low degree of contrast indicates a low degree of subsurface light diverting structure in the tooth subjacent the illuminated area. The significance of relative degrees of contrast is discussed hereinafter.

Figure 11:
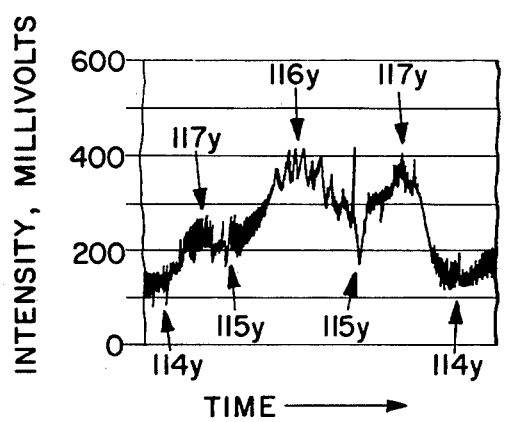
FIGS. 11 and 12 are views of strip chart recorded data obtained by scanning a 6-hour calibration standard, Table 1, and a 72-hour calibration standard, respectively, through the use of the instrumentation system shown in FIG. 9 while the calibration standards were illuminated as indicated in FIG. 10.
Figure 12:
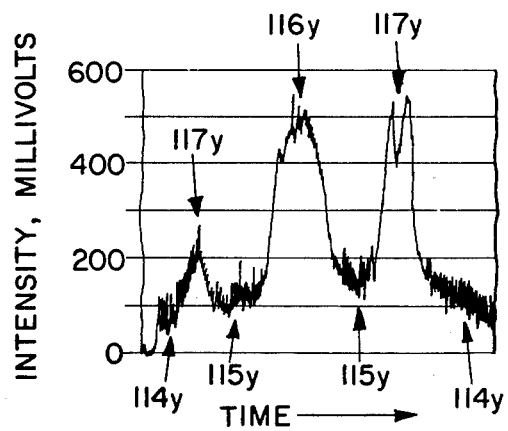

The video control unit 52, FIG. 1, and the computer units 60 and 61 also enable the system operator to generate a scan line 130 in any predetermined position with respect to the image pattern on the video monitor 56. Moreover, the scan rate or rate of scanning along the scan line is controllable/programmable from relatively slow (e.g. several seconds) to relatively fast (e.g. milliseconds). Preferably, the scan line 130 is vertical as shown in FIG. 1 and crosses the image pattern diametrically. Thus, when a scan is initiated by operating scan switch 53, an electrical signal which is proportional to the brightness on the video monitor along the scan line 130 will be forwarded to the strip chart recorder 58 via cable 63f, and to the digital computer 60 via cable 63j. As indicated in FIGS. 11 and 12 which are fully described hereinafter, shadow zones such as the shadow ring 115r are seen as low amplitude valley positions, and the lighted zones such as the light circle 116r and the light ring 117r are seen as high amplitude peaks. The strip chart recording enables manual reduction of the contrast data along the scan line 130 whereas the computer 60 enables the data to be reduced automatically in accordance with however the computer 60 is programmed. The inherent slowness of strip chart recorders relative to digital computers limits the use of the strip chart recorder 57 in system 40 to relatively slow scan rates.

Briefly, when the instrumentation system 40, FIG. 1, comprises an optical probe 41a, FIG. 2, and is operated by a user such as, for instance, a dentist, to conduct in vivo dental examinations, the nose of the probe would be placed against a surface of a tooth to be examined. Of course, the resilient tubular member 96, FIG. 2, obscures the dentist's view. Thus, the closed circuit video system provides the user with indirect visual contact with the surface the probe is against. The dentist then presses the nose of the probe against the surface to be examined with sufficient force to provide a focused image on the video monitor. The nose of the probe is then moved about the surface to locate zones of the surface which produce relatively high intensity areas on the screen of the video monitor. When such a zone is located, the probe is moved to position the brightest portion of the bright zone in the centrally disposed circular area 116r on the video monitor 56. With the probe so positioned and focused, a scan along line 130 is initiated by operating scan switch 53, FIG. 1. The video intensity data along line 130 is then forwarded to the strip chart recorder 57, or the digital computer 60 for recordation or processing. Alternatively a permanent picture of the image on the video monitor can be generated by triggering the hard copy printer 58. Thus, zones the anomalous subsurface structure (e.g., pre-carious lesions) can be identified and relatively quantified. The relative brightness of light zones on the video monitor correlates with the degree of seriousness of pre-carious lesions. This is described in more detail hereinafter.

Figure 6:
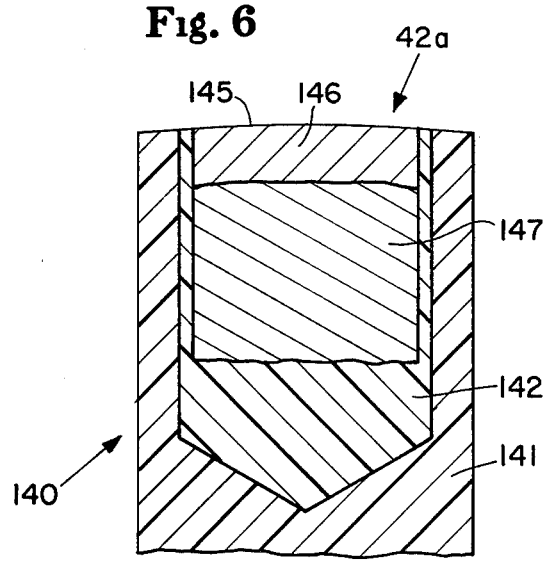
FIG. 6 is a fragmentary, side elevational sectional view of a calibration standard through the use of a plurality of which standards, apparatus embodiments of the present invention can be calibrated.

FIG. 6 is a longitudinal sectional view of a calibration standard 140 through the use of a plurality of which the system 40, FIG. 1, can be empirically calibrated as hereinafter described.

The calibration standard 140, FIG. 6, comprises a 4 millimeter diameter cylindrical portion 42a of a sound tooth, a 6 millimeter diameter Plexiglas (trademark, E.I. DuPont Co.) rod 141, and an adhesive filler 142 such as Dura Base, a product available from Reliance Dental Mfg. Co., Chicago, Ill. The tooth portion 42a comprises a cleaned and polished original outer surface area 145, enamel 146, and dentin 147; reference the Dental Science Handbook, DHEW Publication No. (NIH) 72336 which was edited by Lon W. Morrey, D.D.S., and by Robert J. Nelsen, D.D.S. which publication has been assigned Library of Congress Catalog Number: 75-603909.

Quasi pre-carious lesions of various degrees are induced in a plurality of calibration standards 140 constructed in accordance with FIG. 6. This is done by exposing for various time periods, the outer surface 145 of the tooth portion 42a to an etching solution comprising sufficient lactic acid having a 0.5 M lactate concentration to reduce the concentration of a 0.002 M aqueous solution of $Na_2H_2MDHP$ (disodium dihydrogen methanehydroxydiphosphonate) to a 0.0001 M concentration and which mixture is buffered with sufficient NaOH (sodium hydroxide) to provide a pH of 4.50. An alternative similar method of inducing white spots on teeth is described in an article Hard Tissue Growth, Repair, and Remineralization, Ciba Foundation Symposium II (new series) published 1973 by ASP (Elsevier Excerpta Medica North-Holland), Amsterdam.

Because of the smallness of a pre-carious lesion, the relative degree of the quasi pre-carious lesion induced in each standard is inferred from quantitative chemical analysis of the etching solution to determine the weight loss suffered by the standard as a result of being etched. The weight loss is then converted to nominal void volumes using nominal density values for the constituents of teeth. Table 1 lists a number of standards, their respective etching periods, and their respective inferred average void volumes in nanoliters which standards were prepared (etched) in batches of three standards each. These standards are referred to herein as 6-hour, and 72-hour calibration standards, and the like.

TABLE 1

| CHIP # | ETCHING PERIOD | AVERAGE VOID VOLUME IN NANOLITERS |
|---|---|---|
| 10871 thru 3 | 6 hours | 63.4 |
| 10881 thru 3 | 12 hours | 103.9 |
| 10891 thru 3 | 24 hours | 192.8 |
| 10901 thru 3 | 36 hours | 275.5 |
| 10911 thru 3 | 48 hours | 314.2 |
| 10921 thru 3 | 72 hours | 415.8 |

FIG. 7 is a greatly enlarged scale, fragmentary longitudinal sectional view of a somewhat schematic representation of a portion 42a of a sound tooth such as shown in FIG. 6 which has an original outer surface area 145, which is very smooth. FIG. 7 shows a sound tooth structure to comprise a multiplicity of enamel rods 150 having nominal diameters DR of about 4 microns, and which structure has elongate interstices 151 disposed between the rods 150. In sound enamel, the interstices 151 have nominal widths IS of about 0.002 microns. When oblique rays of incident light impinge on the outer surface 145 of such a sound tooth portion as indicated by arrows 152 having an oblique incident angle 153, most of the light is specularly reflected as indicated by arrows 154 having an angle of reflection 155 equal to the incident 153. Very little diffuse surface reflection occurs because of the smoothness of the tooth's surface 145. However, as indicated by the inwardly directed arrows 157, some of the incident light penetrates into the interior of the tooth and, as indicated by arrows 158, may be internally reflected or otherwise internally diverted but still continues penetrating generally downwardly and, perhaps somewhat laterally. Thus, as stated hereinbefore, a sound tooth exhibits little upwardly/outwardly directed internally diverted light when obliquely illuminated as indicated by arrows 152 in FIG. 7 because, it is believed, there is a relative dirth of internal interfaces in sound tooth structure which are so oriented as to precipitate upwardly/outwardly directed internally diverted light.

Figure 8:
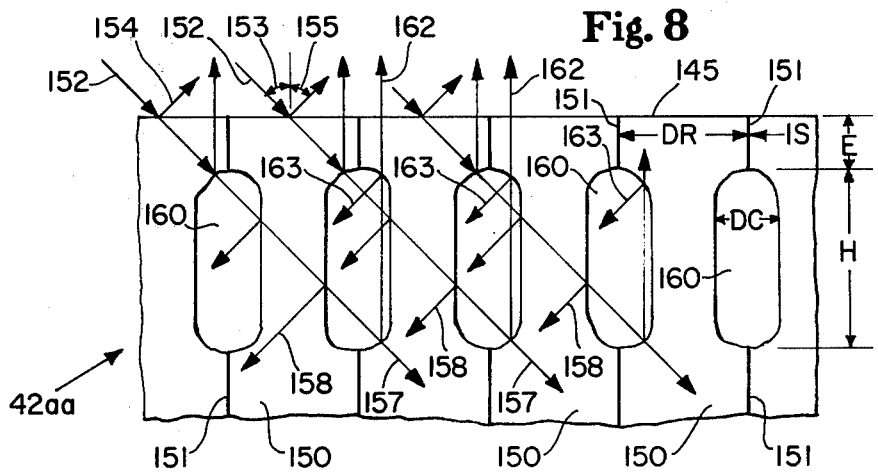

FIG. 8 is a greatly enlarged scale, fragmentary longitudinal sectional view of a somewhat schematic representation of a portion designated 42aa of a tooth such as shown in FIG. 6 which portion 42aa has had quasi precarious lesions induced subjacent its original surface 145 by the etching method described hereinabove. The etching enlarges the widths IS of the elongate interstices 151 up to about 0.01 microns, and induces the formation of a zone of minute subsurface voids 160 (i.e., a quasi pre-carious lesion) having widths DC of up to one or two microns and dimensions H of up to about 30 to 50 microns. The voids 160 are spaced a distance E below surface 145. Distance E may be from about 5 to about 10 microns. Thus, the surface 145 remains relatively sound and highly reflective but becomes undermined by the zone of voids 160; that is, by a quasi pre-carious lesion.

Still referring to FIG. 8, the voids 160 provide internal interfaces in the tooth which can precipitate outwardly directed, internally diverted light, as indicated by arrows 162, when the tooth is illuminated as described above in conjunction with describing FIG. 7. As further indicated by arrow 163, the voids 160 may also incidentally provide additional inwardly directed internally diverted light.

To summarize that which is shown in FIGS. 7 and 8, and described hereinabove, a sound tooth will exhibit relatively little outwardly directed, internally diverted light when illuminated by an oblique light beam whereas a tooth having anomalous subsurface structure such as a precarious lesion will exhibit greater amounts of such outwardly directed, internally diverted light. The relative intensity of such internally diverted light correlates with the degree of subsurface anomalous structure as will be described hereinafter in conjunction with discussing FIG. 13.

System 40, FIG. 1, is calibrated in the manner described below with respect to alternate instrumentation system 40b, FIG. 9.

Figure 9:
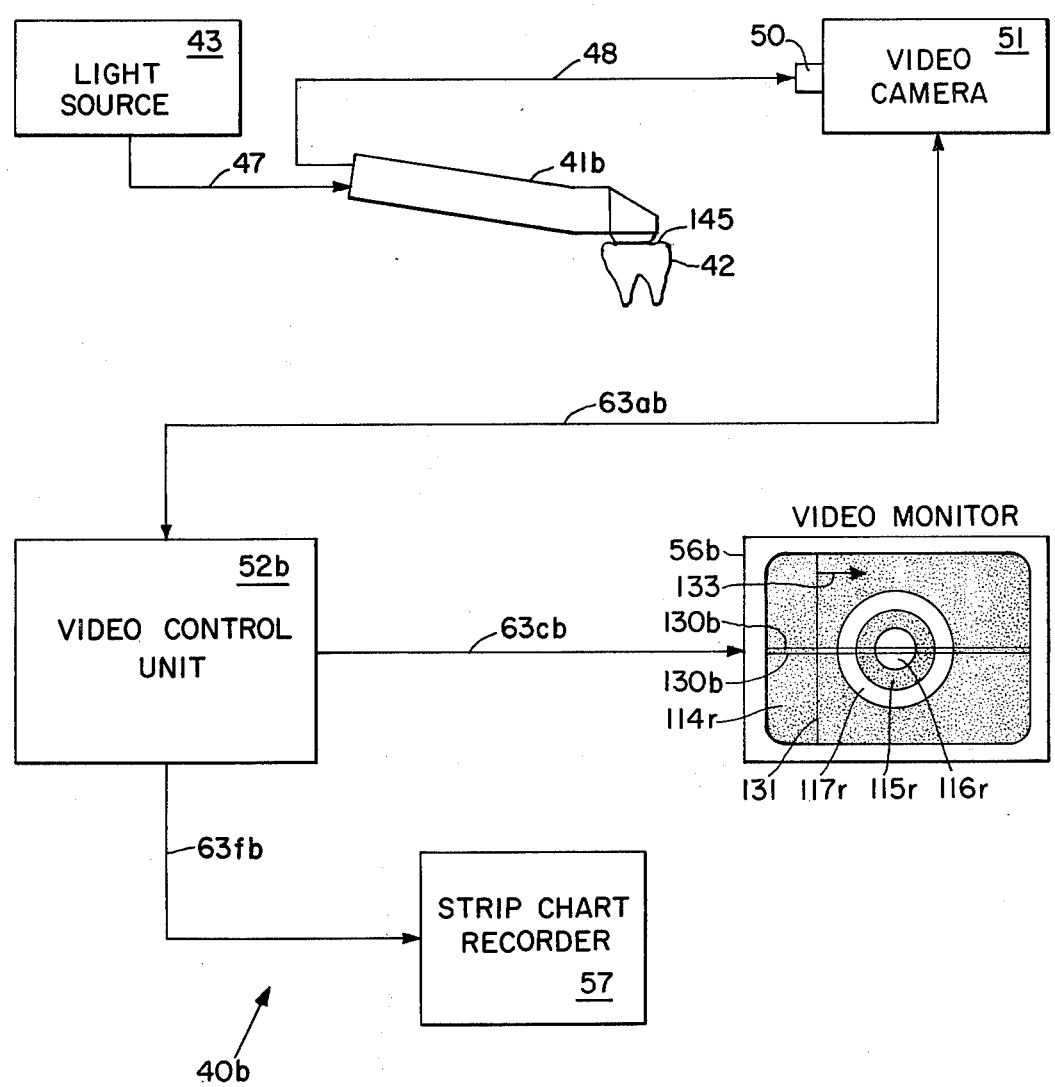
FIG. 9 is a block diagram of an alternate embodiment optical instrumentation system comprising an alternate embodiment optical probe similar to that shown in FIG. 2.

An alternate instrumentation system 40b which is constructed in accordance with the present invention is shown in FIG. 9 to comprise a light source 43, an incoherent fiber optic cable 47, an optical probe 41b, a coherent fiber optic cable 48, a video relay lens 50, a video camera 51, a video control unit 52b, a video monitor 56b, a strip chart recorder 57, and cables 63ab, 63cb, and 63fb. In a representative system 40b, the light source 43 is a Model 8 available from Skia Corp., 460 Division Street, Campbell, Calif., 95008; fiber optic cables 47 and 48 are the same as identified hereinbefore in system 40; the video camera 51 is Model 501A available from Colorado Video Inc.; the video control unit 52b comprises a Krohn-Hite Function Generator, Model 5100AR, and a Model 302 Video Analyzer, a Model 604 Video Processor, and a Model 601B Synchronizing Generator from Colorado Video Inc.; and the video monitor 56b is a Model RCL14 available from Conrac Corp., Covina, Calif. The cables 63ab, 63cb, and 63fb are constructed to provide means for coupling the members of the system together so that the system can be operated as described below.

The probe 41b, FIG. 9, is substantially identical to probe 41a, FIG. 2, except probe 41b does not include a circularly-polarizing filter 93, and its optical members are not anti-reflective coated. However, the probe 41b is operated in the same manner as probe 41a and therefore its operation will not be described again.

The video subsystem of system 40b comprises camera 51, control unit 52b, and monitor 56b. The video subsystem provides the same output picture as the video portion of system 40 but, whereas system 40 has a scan switch 53, FIG. 1, system 40b continuously sequentially sweeps a quasi raster comprising a plurality of horizontal scan lines 130b along a vertical sweep line 131 which sweep line moves horizontally as indicated by arrow 133. That is, the scan lines 130b are stationary whereas the sweep line 131 cyclically moves across the screen of the video monitor.

Figure 10:
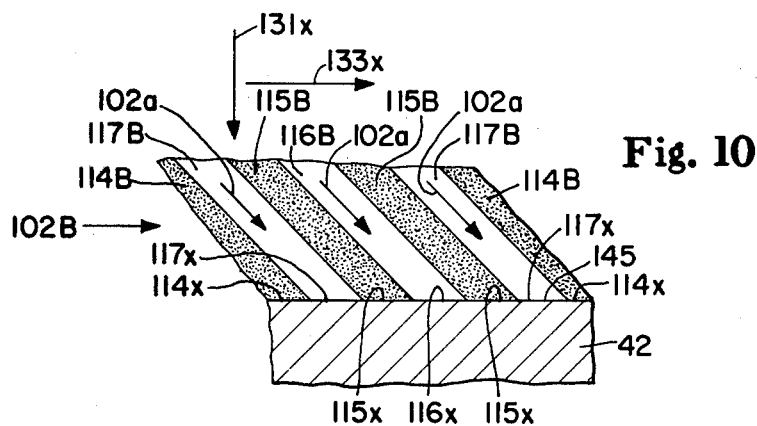
FIG. 10 is a fragmentary, enlarged scale, sectional view of an article such as a tooth having its top surface illuminated by a patterned light beam such as produced by passing a beam of light through the reticle shown in FIG. 3 which reticle is disposed in the optical probe, FIG. 2.

In the operation of system 40b, FIG. 9, a portion of the top surface 145 of a translucent tooth 42 is illuminated as indicated in FIG. 10 by an oblique beam 102B of light of oblique rays designated 102a. Beam 102B comprises central shaft 116B, and an annular tubular shaft of light 117B which are spaced by a tubular shadow 115B. The annular tubular shaft of light 117B is bounded by shadow 114B. Beam 102B is produced as described hereinbefore by passing light through a reticle 82, FIGS. 3 through 5, inclusive. Arrow 131x in FIG. 10 represents a line-of-sight of the video system which line-of-sight is moved in the direction indicated by arrow 133x. This corresponds directly with the movement of sweep line 131 on the video monitor 56b, FIG. 9, as indicated by arrow 133. Also, the illuminated and shadow areas of surface 145, FIG. 10, correspond to the lighted and shaded areas of the picture on the video monitor 56b, FIG. 9, except in FIG. 10 the corresponding numbers have x suffixes rather than r suffixes. That is, areas 114r through 117r on FIG. 9 correspond with areas 114x through 117x, FIG. 10.

In operation, an electrical signal which is proportional to the average intensity of light along the scan lines 130b, FIG. 9, is forwarded to the strip chart recorder 57 as the vertical sweep line 131 moves, as a function of time, from side to side as indicated by arrow 133.

FIG. 11 is a fragmentary portion of a strip chart recording resulting from illuminating a surface area 145 of a 6-hour calibration standard, Table 1, and sweeping line 131, FIG. 9, (line of sight 131x, FIG. 10) across the video monitor 56b, FIG. 9, during which sweep, line 131 sequentially crosses a first segment of shadow 114r, a first segment of light ring 117r, a first segment of shadow ring 115r, light circle 116r, a second segment of shadow ring 115r, a second segment of light ring 117r, and a second segment of shadow 114r which correspond respectively to the shadow 114x, light ring 117x, shadow ring 115x, light circle 116x, shadow ring 115x light ring 117x, and shadow 114x on FIG. 10, and which also correspond respectively to the peaks and valleys shown in FIG. 11 and identified by corresponding numbers with y suffixes, to wit: shoulder 114y, peak 117y, valley 115y, peak 116y, valley 115y, peak 117y, and shoulder 114y, respectively. Since both the sweep line 131, and the strip chart recordr paper move in fixed time relation, FIG. 11 is, effectively an x-y plot wherein the x axis (the TIME axis) represents the horizontal position of sweep line 131 on FIG. 9, and the y axis is the point-by-point intensity of light received by the video system (along the line-of-sight 131x, FIG. 10) as a sweep occurs. Indeed, the strip chart recorder 57 can be replaced by an x-y recorder by feeding its x axis channel with a signal proportional to the horizontal sweep signal in the video monitor, and by connecting its y axis to the present data signal output which is proportional to the video intensity signal on the video monitor 56b.

FIG. 12 corresponds to FIG. 11 except FIG. 11 was obtained by illuminating (inspecting) a 6-hour calibration standard, Table 1, whereas FIG. 12 was obtained by illuminating (inspecting) a 72-hour calibration standard. Thus, the relatively large quasi pre-carious lesion in the 72-hour standard results in greater peak-to-valley differences, FIG. 12, than the relatively minor quasi pre-carious lesion in the 6-hour sample, FIG. 11.

Figure 13:
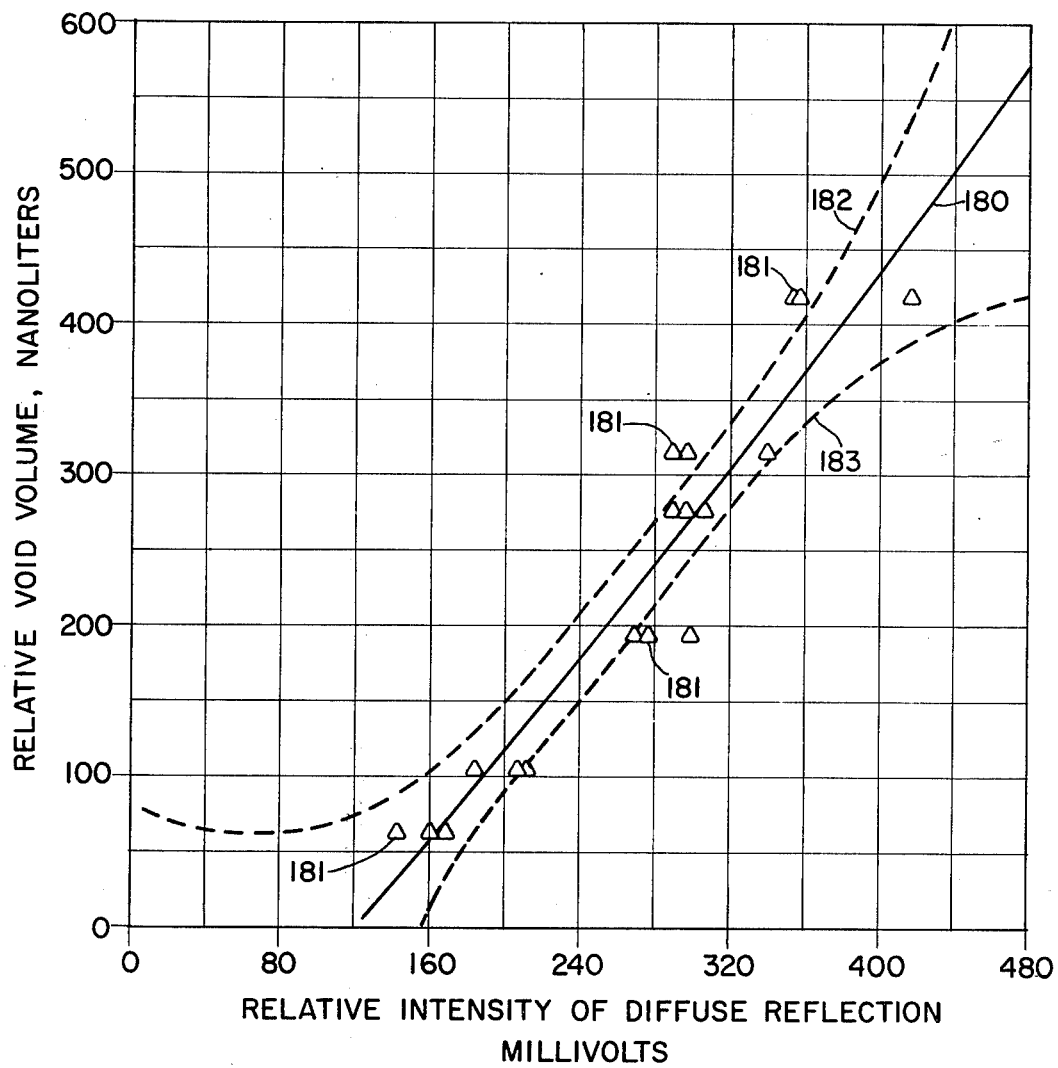
FIG. 13 is a graph showing an empirical calibration curve for the instrumentation system shown in FIG. 9.

FIG. 13 is a graph showing a calibration curve 180 for alternate system 40b which was obtained by inspecting the calibration standards listed in Table 1, and by reducing the resulting strip chart data (like that shown in FIGS. 11 and 12) by subtracting the average of both valleys 115y, from the central peak 116y to obtain the discrete data points 181, FIG. 13. This data was then statistically analyzed to compute and plot a best fit curve 180 and the related ninety-five percent (95%) confidence limits; the dashed lines 182 and 183 on FIG. 13.

Figure 14:
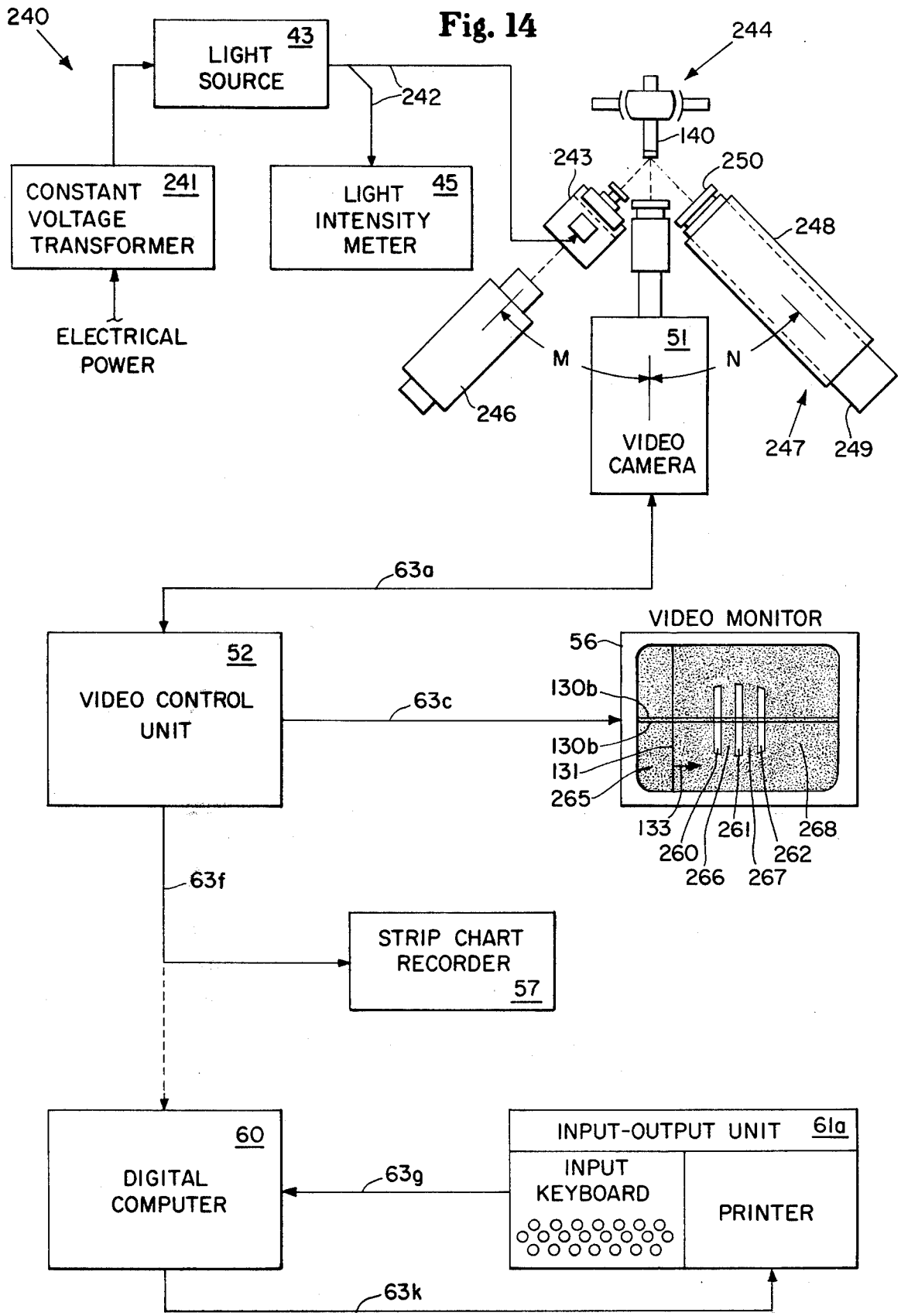
FIG. 14 is a block diagram of a bench type instrumentation system embodying the present invention.

FIG. 14 is a block diagram of a bench type instrumentation system 240 constructed in accordance with the present invention and in which the same designators are used for elements which correspond to the elements of system 40, FIG. 1, and/or system 40b, FIG. 9. However, whereas the INPUT-OUTPUT UNIT 61 of system 40, FIG. 1, comprised an Input Keyboard and a CRT Display Module, the INPUT-OUTPUT UNIT of system 240 is designated 61a inasmuch as it comprises an Input Keyboard in combination with a Printer. Such a unit may be, for instance, a Teletype Model 33TU available from the Teletype Corporation, Skokie, Ill. To obviate undue redundancy, system 240 will be described in terms of difference with respect to systems 40, and 40b.

As compared to system 40, FIG. 1, system 240, FIG. 14, additionally comprises a constant voltage transformer 241, a y-shape incoherent fiber optic cable 242, an incident light beam projection means 243, an x-y-z-azmuth-elevation positioner 244 for holding and positioning a test article such as a calibration standard 140, FIG. 6, and a laser 246 and a sighting tube assembly 247 for optically aligning the system to provide a forty-five (45) degree incident angle M, and a forty-five (45) degree angle of reflection N. This alignment is made with the fiber optic cable 242 unplugged from the projection means 243 so that the laser beam can pass through the projection means 243.

The constant voltage transformer 241, FIG. 14, is provided to stabilize the output intensity of the light source 43.

The y-shape fiber optic cable 242, FIG. 14 is a unitary structure which is functionally equivalent to fiber optic cables 46 and 47 of system 40, FIG. 1.

The sighting tube assembly 247, FIG. 14, comprises a fixed hollow tube 248 and a moveable hollow tube 249 which is telescoped into tube 248. A ground glass viewing screen 250 is provided in the end of tube 249 disposed close to the calibration standard 140. When the standard 140 is properly positioned and illuminated by laser 246, the specularly reflected light illuminates a spot on the screen 250. The spot on screen 250 will appear to be fixed on screen 250 as the tube 249 is moved inwardly and outwardly; if the standard 140 is not properly positioned, the spot will appear to move on screen 250.

The projection means 243 comprises a reticle (not shown) having a pattern of alternately spaced parallel transparent areas and opaque areas on a flat glass blank as compared to the pattern of concentric circles on reticle 82, FIGS. 3 through 5 inclusive. Thus, the picture on the video monitor comprises 3 vertical light bars 260, 261, and 262; and shadow areas 265, 266, 267, and 268.

As described in conjunction with system 40b, FIG. 9, a plurality of scan lines 130b extend horizontally across the light/shadow pattern, and a vertical sweep line 131 is horizontally moveable as indicated by arrow 133.

In operation, a surface area of interest of a test translucent article (e.g., a calibration standard 140, FIG. 6) is illuminated by an oblique, image carrying incident light beam, and the closed circuit video system views the illuminated area along a line-of-sight which is normal to the surface area of interest. As the sweep line 131 passes over the picture (image) on the video monitor 56, a signal which is proportional to the average video (light) intensity along the scan lines 130b is forwarded to the strip chart recorder 57. Alternatively, the signal could be forwarded to the digital computer for automatic data processing as described hereinbefore. This alternative is illustrated by the dotted line connection of cable 63f to the digital computer 60.

Figure 15:
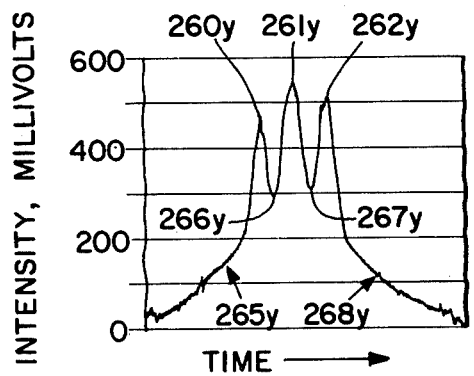
FIGS. 15 and 16 are views similar to FIGS. 11 and 12 of strip chart recorded data obtained through the use of the bench type instrumentation system shown in FIG. 14.
Figure 16:
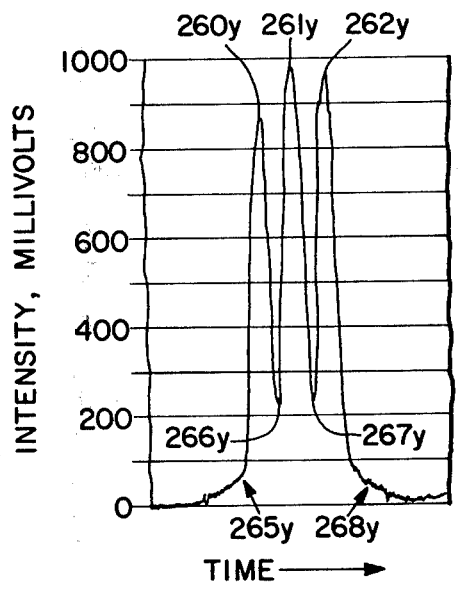

FIGS. 15 and 16 illustrate exemplary strip chart recordings which were produced by inspecting 6-hour and 72-hour calibration standards, Table 1 and FIG. 6, comprising relatively minor and major quasi pre-carious lesions, respectively. The portions of the recorded signal corresponding to the light bars and shadow areas identified in FIG. 14, are identically numbered and have y suffixes. Briefly, the peaks correspond to the light bars, and the low ends and valleys correspond to the shadow areas, as was described hereinbefore in conjunction with FIGS. 11 and 12. The difference in relative intensity between FIGS. 15 and 16 on the one hand, and FIGS. 11 and 12 on the other hand reflect a greater intensity of light in the bench system 240, FIG. 14, as compared to the probe-type system, 40b, FIG. 9. Of course, additional intensity can be provided in the probe system 40b by means well known to persons of ordinary skill in the art.

Figure 17:
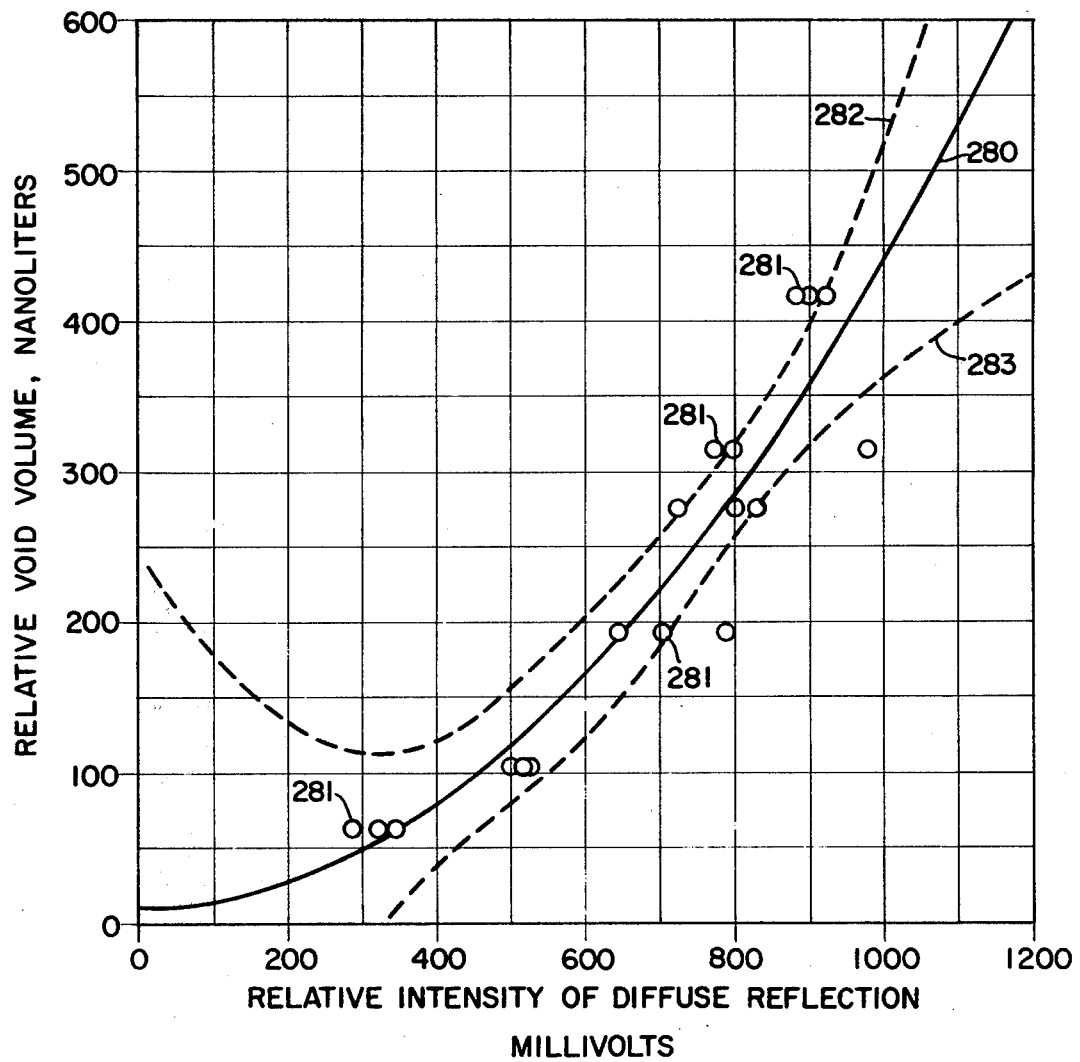
FIG. 17 is a graph showing an empirical calibration curve for the instrumentation system shown in FIG. 14.

FIG. 17 is a graph showing a calibration curve 280 obtained in the manner described in conjunction with FIG. 13 through the use of the calibration standards 140 listed in Table 1. Discrete data points are designated 281. Curve 280 is a best fit curve with respect to data points 281, and lines 282 and 283 are ninety-five percent (95%) confidence limits.

Figure 18:
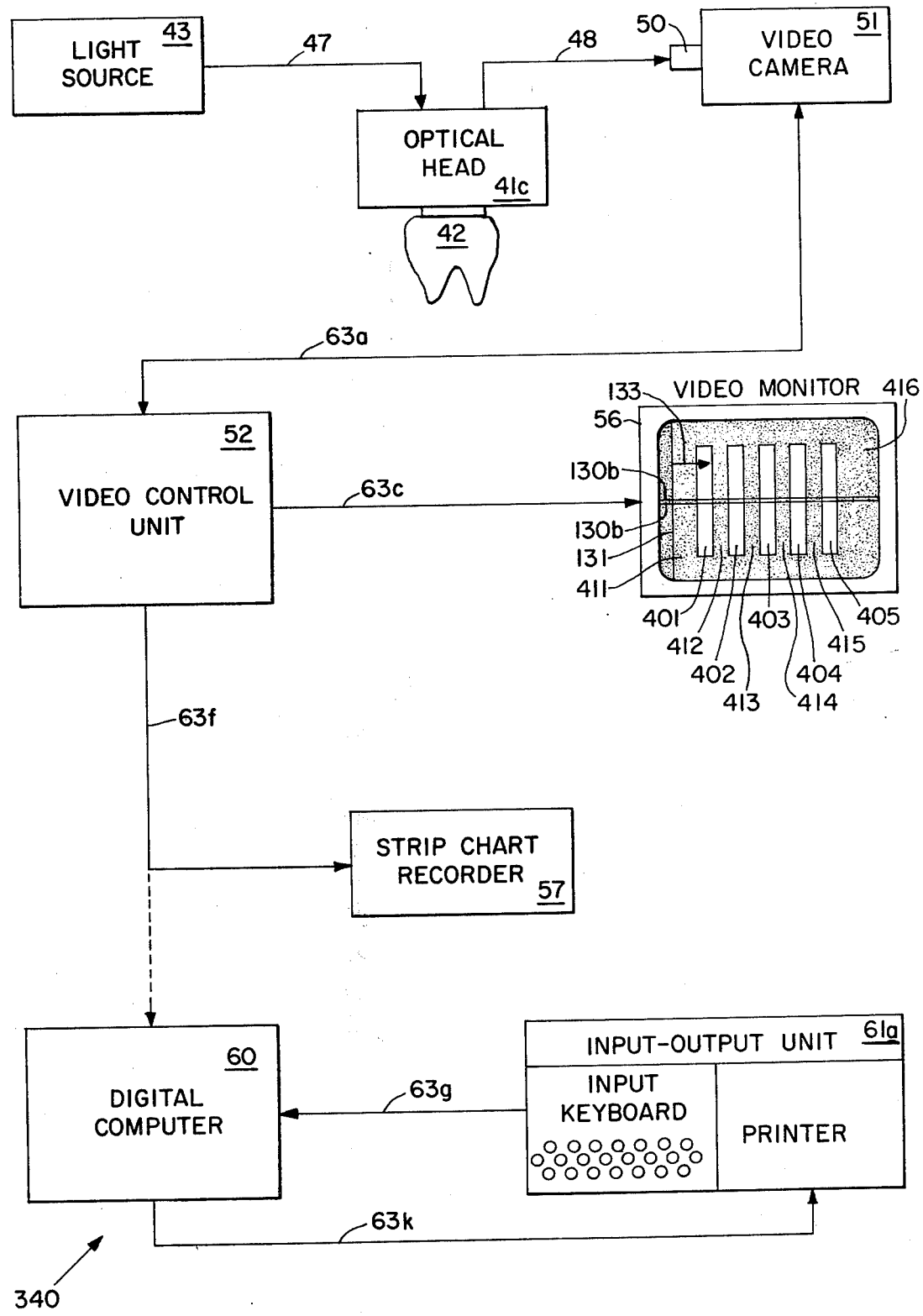
FIG. 18 is a block diagram of another alternate instrumentation system comprising another alternate embodiment optical probe or head.

FIG. 18 is a block diagram of an alternate probe-type instrumentation system 340 constructed in accordance with the present invention.

System 340, FIG. 18, is a hybrid of system 40b, FIG. 9, and system 240, FIG. 14, wherein the optical head 41c is an alternate optical probe 41c, FIGS. 19 through 21 inclusive.

Alternate probe 41c, FIG. 19, comprises two tubes 342 and 343, two yokes 344 and 345, and means for having fiber optic cables 47, 48 connected thereto. Tube 342 is provided with two holes 346 and 347. Hole 346 is provided for visual inspection of the probe's reticle, and hole 347 is a passageway for projecting an incident light beam 348, FIG. 20, onto the surface 145 of an article 349 such as a calibration standard 140, FIG. 6. Tube 343 is provided with a hole 350 through which the video camera 51 of system 340, FIG. 18, can view the surface 145 of the article 349 illuminated by the incident light beam 348 by looking along a line of sight V, FIG. 20, which is normal to the illuminated surface 145.

FIG. 21 is a sectional view which shows the internal elements of probe 41c to comprise lenses 351 through 358, reticle 360, aperture discs 361 and 362, and front surface mirrors 363 and 364 which perform the functions of the corresponding members of probe 41a, FIG. 2.

Reticle 360, FIG. 21, is shown in FIGS. 22 and 23 to comprise parallel alternately spaced opaque bars 366 and transparent areas 367 on an optically flat glass blank 368.

FIG. 24 is a fragmentary perspective view of an article 349 having parallel bar-shape areas 370 of its surface 145 illuminated by probe 41c, and showing parallel shadow bars 371 between the lighted bars 370. Arrow 373 represents an exemplary ray of the incident light beam 348, FIG. 20, and the resulting specularly reflected ray is represented by arrow 374. The angles designated 381, 382, and 383 in FIG. 24 are right angles and define a plane 386 and line 387 which are both normal to surface 145. Arrows (rays) 373 and 374 lie in plane 386 and, of course, the incident angle 391 is equal to the angle of reflection 392. Both angle 391 and angle 392 are preferably forty-five (45) degrees in probe 41c. Also, in probe 41c, there are fifty (50) line pairs per inch on reticle 360. That is, each opaque bar 366 and each transparent area 367 are ten-thousandths of an inch wide.

Referring back to FIG. 18, the picture on the video monitor 56 comprises five vertically oriented light bars 401 through 405, shaded areas 411 through 416, stationary scan lines 130b, movable sweep line 131, and arrow 133 indicates the direction of movement of sweep line 131. As in systems 40b, and 240, sweeping (movement) of line 131 is continuous.

Figure 25:
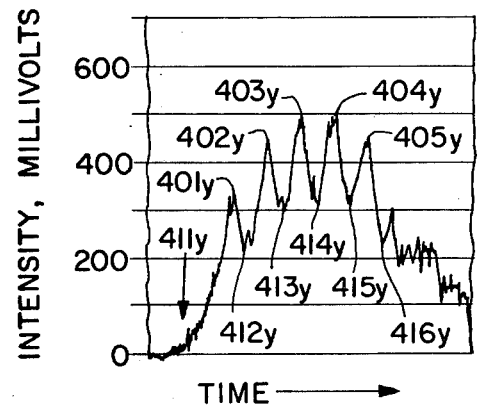
FIGS. 25 and 26 are views similar to FIGS. 11 and 12, and FIGS. 15 and 16 of strip chart recorded data obtained through the use of the instrumentation system shown in FIG. 18, and the optical probe shown in FIGS. 19 through 21 inclusive.
Figure 26:
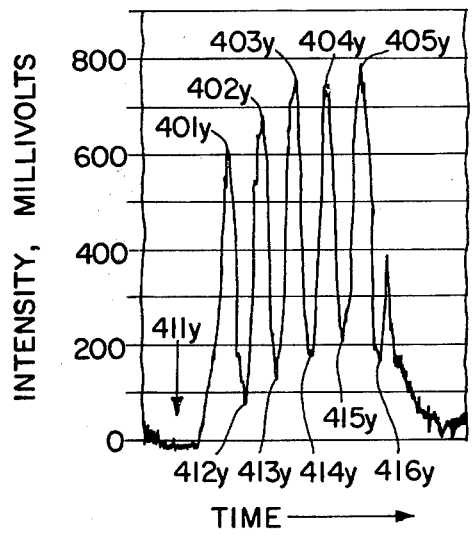

FIGS. 25 and 26 are representative strip chart recordings of data taken by system 340 while inspecting 6-hour and 72-hour calibration standards, Table 1 and FIG. 6, having relatively minor and major quasi precarious lesions, respectively, as previously described in conjunction with FIGS. 11 and 12, and FIGS. 15 and 16. The peaks and valleys on the strip chart recordings, FIGS. 25 and 26, are numbered the same as the corresponding light bars 401 through 405 and shaded areas 411 through 416, FIG. 18, with the suffix y added.

Figure 27:
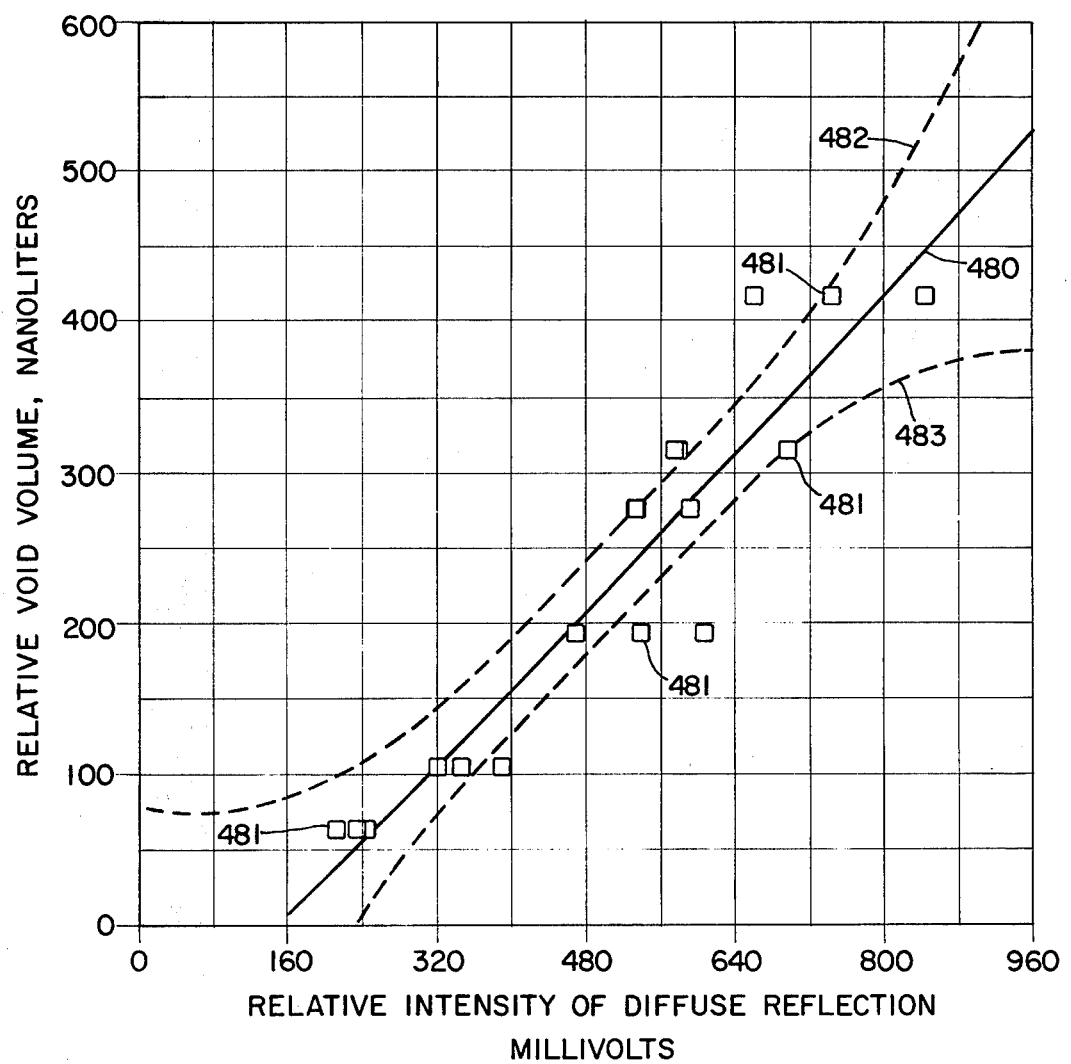
FIG. 27 is a graph showing an empirical calibration curve for the optical instrumentation system shown in FIG. 18 which system comprises the optical probe shown in FIGS. 19 through 21 inclusive.

FIG. 27 is a graph showing a best-fit calibration curve 480 for system 340, discrete data points 481, and ninety-five percent (95%) confidence limit lines 482 and 483. FIG. 27 was developed by examining the calibration standards listed in Table 1 with alternate system 340, FIG. 18.

Figure 28:
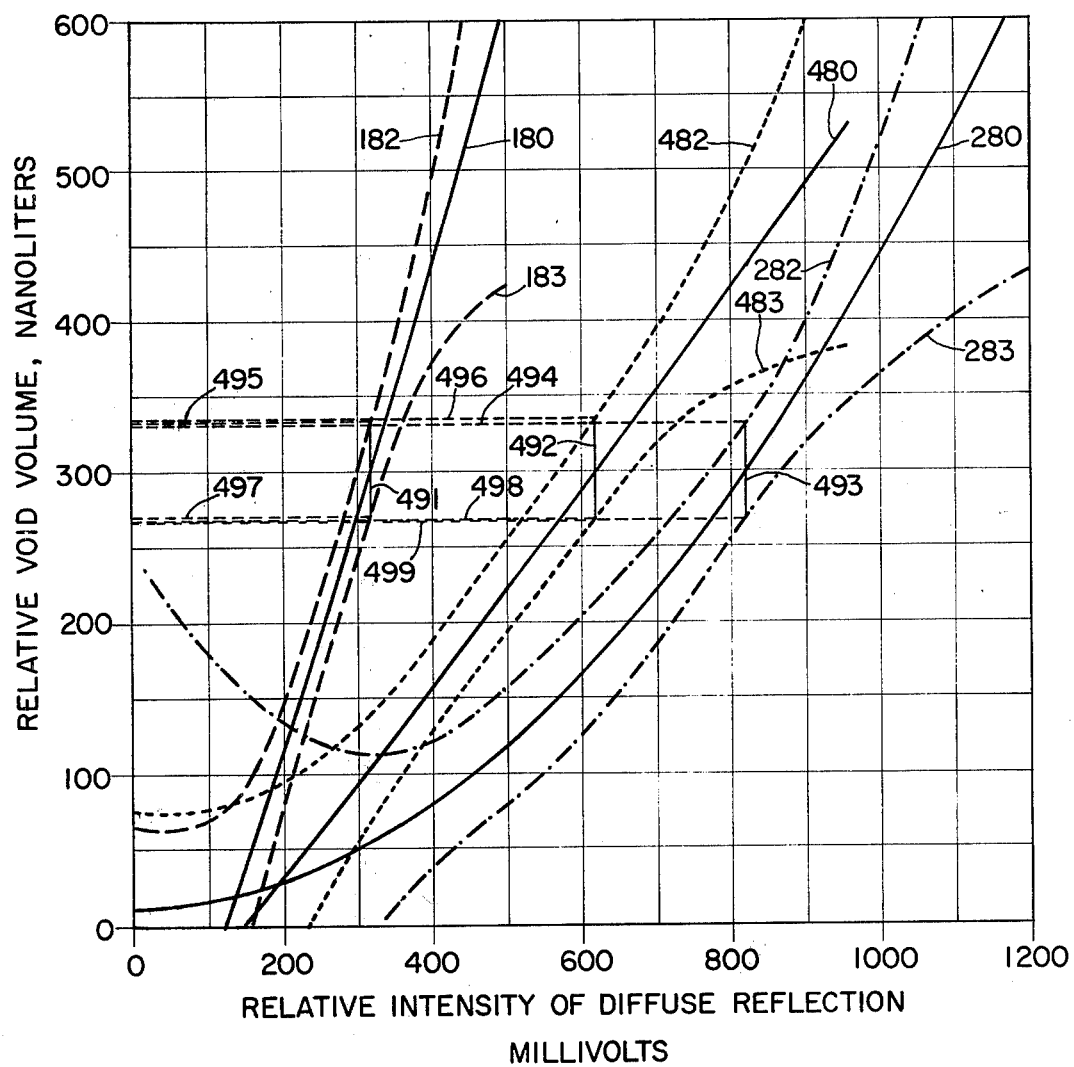
FIG. 28 is a composite graph showing the calibration curves of FIGS. 13, 17, and 27, and their respective computer-derived, ninety-five percent (95%) confidence limits.

FIG. 28 is a composite graph which combines the calibration curves and ninety-five percent (95%) confidence limit lines of FIGS. 13, 17, and 27. As indicated by the verticle lines 491, 492 and 493, and the dashed horizontal lines 494 through 499, the vertical ranges of relative void volumes between the upper and lower ninety-five percent (95%) confidence limits on systems 40b (FIG. 9), 240 (FIG. 14), and 340 (FIG. 18) are nearly equal for nominal relative void volumes of 300 nanoliters. It is believed that this indicates substantially equal accuracies of the three systems. Moreover, within the range of light intensities used in systems 40b, 240, and 340, the system accuracies are not believed to be critically responsive to or dependent on the absolute light intensity. Thus, it is believed that the systems are relatively insensitive to minor drifts in the intensity of the light output from the light source 43.

FIGS. 29 through 33 show nose portions of alternate optical probe embodiments 541, 641, 741, 841, and 941, respectively for use in optical instrumentation systems such as described hereinbefore. All but probe 741, FIG. 31, comprise additional projection optic means and return optic means to enable the optics to be focused in coincident focal planes, and to enable the probes to be used in the manner described herefore with respect to probes 41a, 41b, and 41c. That is, each will comprise means for projecting incident light which may originate in a remote light source, and means for transmitting returning light to a remote closed circuit video subsystem and/or other light detector means. For instance, such an other light detector means could be a light intensity meter as described hereinafter to which the output of probe 741 could be connected.

Figure 29:
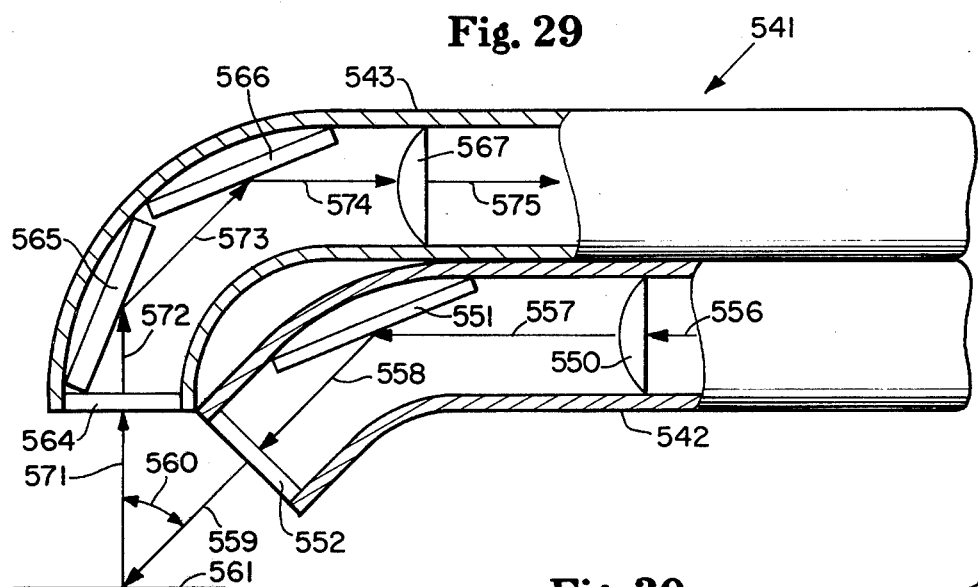
FIGS. 29 through 33 are enlarged scale, fragmentary side elevational sectional views of the nose portions of additional alternate hand-held optical probes constructed in accordance with the present invention.

Probe 541, FIG. 29, comprises over-and-under tubular members 542, 543 with projection optics in member 542, and viewing or return optics in member 543. The projection optics comprise a lens 550, a front surface mirror 551, and an optically flat transparent glass window 552 for transmitting an incident light beam which is indicated by arrows 556 through 559. The focal plane of the projected beam is indicated by line 561, and the angle of incidence 560 is preferably in the range of from about thirty (30) to about sixty (60) degrees, and most preferably is about forty-five (45) degrees.

The viewing optics of probe 541, FIG. 29, comprises an optically flat glass window 564, front surface mirrors 565 and 566, and lens 567 which provide a path for conducting returning light to the viewing system as indicated by arrows 571 through 575. The viewing optics also comprise means for being focused in focal plane 561.

Figure 30:
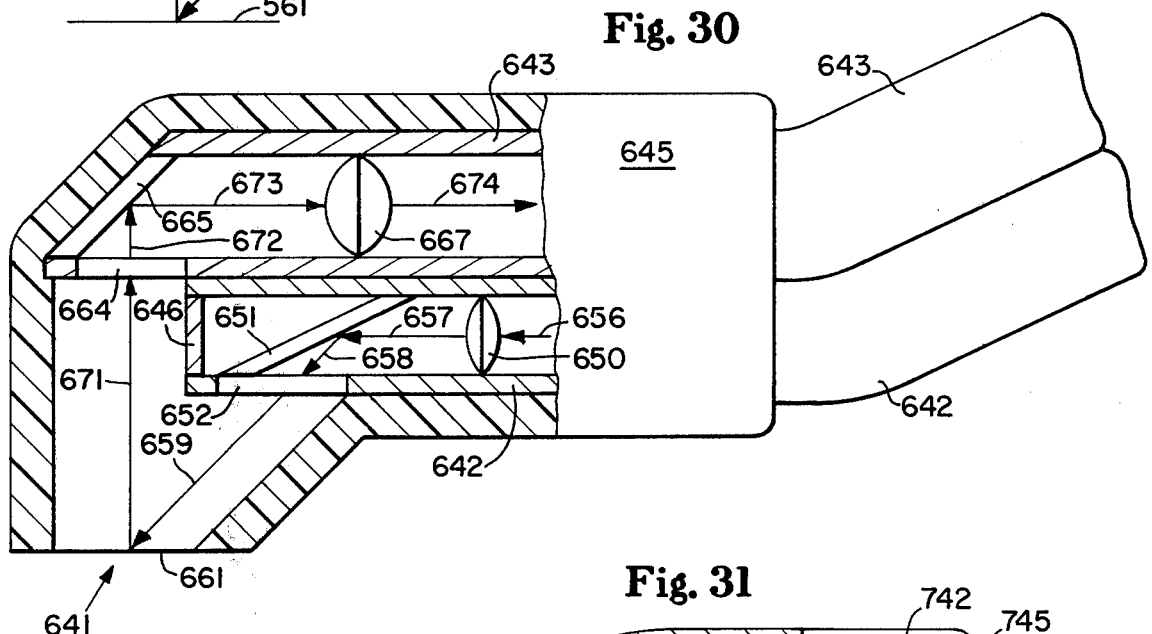

Probe 641, FIG. 30, comprises two tubular members 642 and 643 which are disposed in over-and-under relation. The probe further comprises a nosepiece 645 and a plug 646. Projection optics are contained in tubular member 642 and comprise a lens 650, a front surface mirror 651, and a transparent window 652 which provide a path for an incident light beam along a path indicated by arrows 656 through 659. The focal plane of the incident light beam is coextensive with the distal edge 661 of nosepiece 645.

The viewing optics of probe 641, FIG. 30, comprise a transparent window 664, a front surface mirror 665, and a lens 667 which provide a path for returning light to a viewing system along a path indicated by arrows 671 through 674. The viewing optics further comprise means for being focused in the same focal plane as the projection optics.

Figure 31:
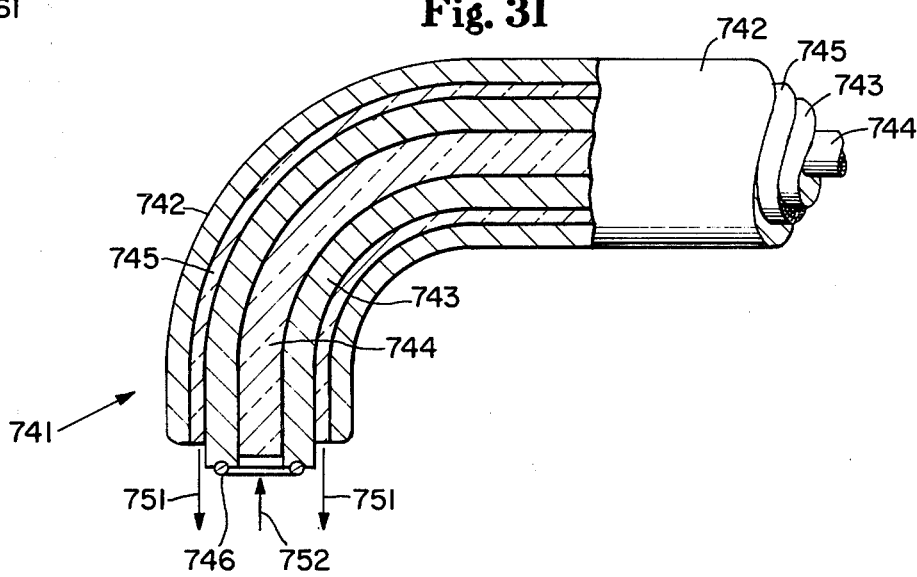

Probe 741, FIG. 31, is a non-image carrying probe which comprises opaque coaxial tubular members 742 and 743, a circular-cross-section fiber optic bundle 744, an annular-cross-section fiber optic bundle 745, and a gasket 746. When the probe is placed with gasket 746 against a surface of interest of a translucent article to be inspected, incident light is conducted via fiber optic bundle 745 and thence along the path indicated by arrows 751. Light which is diverted internally within the article returns to the probe along the path indicated by arrow 752 and thence through the probe via fiber optic bundle 744. Gasket 746 obviates light from entering bundle 744 except by being diverted internally through the article being examined. Of course, as stated hereinbefore, an instrumentation system (not shown) comprising probe 741 does not require a video system. Rather, the fiber optic bundle 744 is simply directed to a suitable light intensity measuring means such as designated 45 in FIG. 1. Alternatively, the light intensity measuring and indicating means as well as a light source could be integrated into a hand-held probe, not shown.

Figure 32:
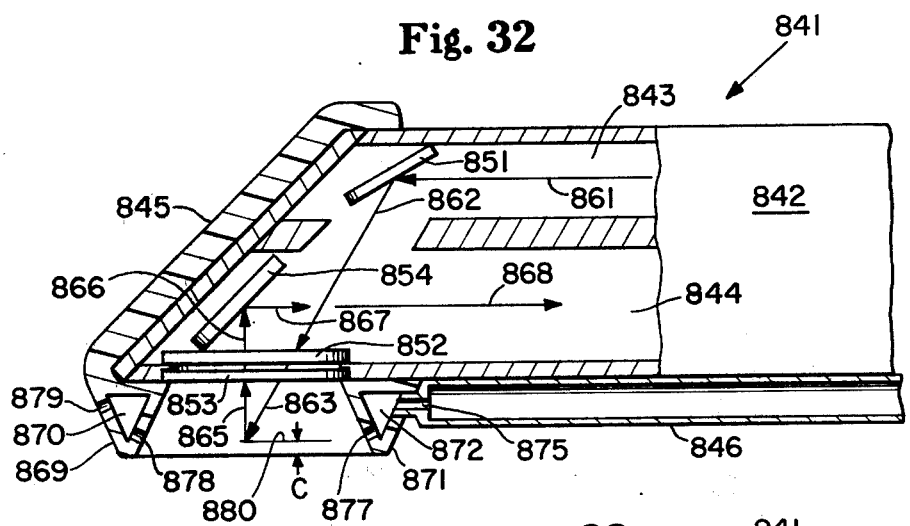

Probe 841, FIG. 32, comprises a body 842 having two longitudinally extending tubular passageways 843 and 844 in over-and-under relation. Probe 841 further comprises a nosepiece 845 and a tubular conduit 846. The optical members comprise an incident-beam front surface mirror 851, circularly-polarizing filter 852, an optically flat glass window 853, and a return-beam front surface mirror 854. The incident light path is indicated by arrows 861, 862, and 863, and the return light path is indicated by arrows 865 through 868.

Nosepiece 845 of probe 841, FIG. 32, is constructed of resilient material and is provided with a hollow front edge 869 having a transverse passageway 870 in it, and a hollow back edge 871 having a transverse passageway 872 in it. The inside of conduit 846 is connected with passageway 872 via passageway 875 to enable forwarding dry air from a source (not shown), through conduit 846, and into passageway 872. Additional holes 877, 878, and 879 are provided to enable the dry air to issue from passageway 872, pass over the surface of an article (not shown) being examined, and then pass into and out of passageway 870 via holes 878 and 879. The optics of probe 841 further comprise means for focusing both the projection optics and the return light optics in a focal plane designated 880 which is spaced a distance C inside the nosepiece 845. Thus, probe 841 comprises means for obviating ambient light, and means for passing a dry gas over a surface of interest normally disposed in focal plane 880 when the probe is manipulated in the manner described hereinbefore in conjunction with probe 41a, FIG. 2.

Figure 33:
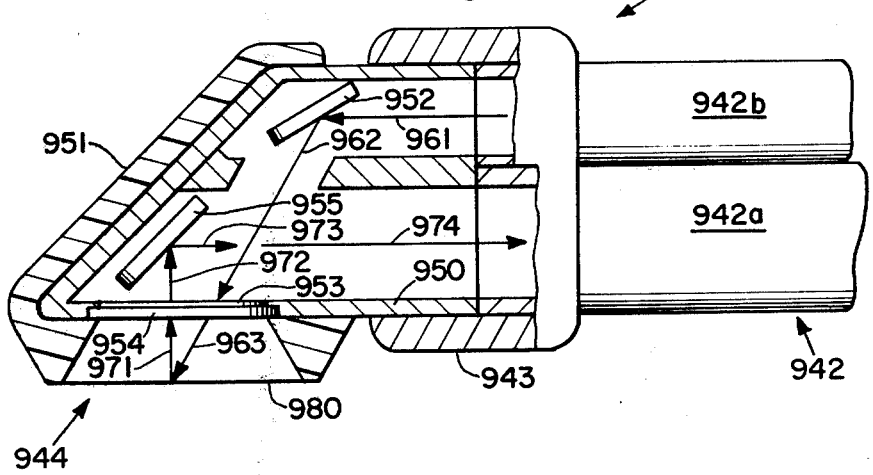

Probe 941, FIG. 33, comprises an over-and-under tubular body 942 comprising tubes 942a and 942b, a coupler 943, and an interchangeable head assembly 944. The interchangeable head assembly comprises a head 950, a nosepiece 951, an incident-light front surface mirror 952, a circularly-polarizing filter 953, an optically flat glass window 954, and a return-light front surface mirror 955. In this probe embodiment, the incident light path is indicated by arrows 961, 962, and 963; and the return light path is indicated by arrows 971 through 974 inclusive. The focal planes of both the projection optics and the return light optics are coextensive with the distal edge 980 of the nosepiece 951.

While particular embodiments of the present invention have been illustrated and described, it would be obvious to those skilled in the art that various other changes and modifications can be made without departing from the spirit and scope of the invention. It is intended to cover in the appended claims all such changes and modifications that are within the scope of this invention. Moreover, as stated hereinbefore, it is not intended to limit the scope of the present invention to the use of light in the visible spectrum.

What is claimed is:

1. A nondestructive method of determining the degree of anomalous subsurface structure of a solid translucent article which method comprises the steps of:
   illuminating a surface area of said article with a beam of incident light of predetermined intensity;
   imposing a predetermined pattern of shaded regions on said incident light beam so that said surface area comprises at least one directly illuminated portion and at least one intervening shaded portion; and
   detecting and quantifying the difference between the intensity of subsurface diverted light emanating from subjacent said directly illuminated portion and the intensity of subsurface diverted said light emanating from subjacent a shaded portion.

2. The method of claim 1 wherein said detecting and quantifying are effected along a scan line extending across said surface area so that said scan line crosses at least one said directly illuminated portion and at least one said shaded portion.

3. The method of claim 2 further comprising the step of inferring from said difference between said intensities the relative degree of subsurface anomalous structure subjacent said illuminated area through the use of an empirical relation between such intensity and the relative degree of subsurface anomalous structure which relation has been derived by making corresponding intensity determinations on a plurality pf graded standards covering a predetermined range of degrees of anomalous subsurface structure.

4. An apparatus for detecting and determining the presence and relative degree of anomalous subsurface structure in a solid translucent article, said apparatus comprising:
   means for illuminating a surface area of said article with a beam of incident light of predetermined intensity;
   means for detecting and quantifying the intensity of a portion of said light which is being internally diverted and emerging outwardly from subjacent said surface area of said article;
   means for inferring from said intensity of said internally diverted light the relative degree of subsurface anomalous structure subjacent said illuminated area through the use of an empirical relation between such intensity and the relative degree of subsurface anomalous structure which relation has been derived by making corresponding intensity determinations on a plurality of graded standards covering a predetermined range of degrees of anomalous subsurface structure; and, means for imposing a shadow pattern image on said beam of incident light and for focusing said image on said surface area to provide at least one directly illuminated portion of said surface area and at least one shaded portion of said surface area, and wherein said means for detecting and quantifying comprises optical viewing means for viewing said surface area and means for scanning said surface area along a scan line which extends across at least one said directly illuminated portion of said surface area and at least one said shaded portion of said surface area, said means for detecting and quantifying further comprising computing means for determining the intensity difference between outwardly directed internally diverted light emerging from said article along the portion of said scan line extending across said directly illuminated portion and the outwardly directed internally diverted light emerging from said article along the portion of said scan line extending across said shaded portion and means for comparing said intensity difference with said empirical relation whereby the relative degree of anomalous subsurface structure in the article can be inferred.

5. The apparatus of claim 4 further comprising means for inferring from said difference the relative degree of subsurface anomalous structure subjacent said illuminated area through the use of an empirical relation between such intensity difference and the relative degree of subsurface anomalous structure which relation has been derived by making corresponding intensity difference determinations on a plurality of graded standards covering a predetermined range of degrees of anomalous subsurface structure.

6. The apparatus of claim 5 further comprising output means for identifying said inferred relative degree of anomalous subsurface structure to an operator of said apparatus.

7. The apparatus of claim 4 further comprising a hand-held optical probe which comprises at least in part said means for illuminating said surface area with a focused image, and said optical viewing means for viewing said focused image.

8. The apparatus of claim 7 wherein said probe further comprises means for obviating from said optical viewing means substantially all of said light which is specularly reflected from said surface area.

9. The apparatus of claim 8 wherein said means for obviating said specularly reflected light comprises means for providing a predetermined incident angle for said incident light which is so related to the angle of acceptance of said viewing means that said specularly reflected light is not received by said viewing means.

10. The apparatus of claim 8 wherein said means for obviating said specularly reflected light comprises means for providing an incident angle for said beam in the range of from about thirty degrees to about sixty degrees, and means for obviating light from said optical viewing means which light has an angle of reflection in the range of from about thirty degrees to about sixty degrees.

11. The apparatus of claim 10 wherein said incident angle is about forty-five degrees, and said optical viewing means has a line of sight which is substantially normal to said illuminated surface area.

12. The apparatus of claim 11 further comprising filter means for obviating diffusely reflected light from said illuminated surface from reaching said optical viewing means which filter means comprises an optical filter for circularly polarizing said incident light, said filter being so disposed that light directed from said illuminated surface towards said optical viewing means must impinge on said filter whereby surface reflections are substantially obviated from reaching said optical viewing means and whereby internally diverted light is not obviated from reaching said optical viewing means.

13. The apparatus of claim 7 wherein said probe further comprises means for obviating from said optical viewing means substantially all of said light which is reflected from said surface area.

14. The apparatus of claim 13 wherein said means for obviating surface reflected light comprises an optical filter for circularly polarizing light which is so disposed that said incident light beam passes through it and upon which filter said surface reflected light directed towards said optical viewing means must impinge.

15. The apparatus of claim 7 wherein said means for focusing said incident light beam on said illuminated surface area comprises a resilient member secured to the nose of said probe so that it can be sufficiently compressed by pressing the nose of said probe against said article to so space said probe from said article that said surface area is in the image plane of said incident light beam.

16. The apparatus of claim 15 wherein said resilient member further comprises a means for obviating ambient light from said illuminated surface area.

17. The apparatus of claim 16 wherein said resilient member further comprises means for conducting a flow of gas across said illuminated surface area.

18. The apparatus of claim 7 wherein said probe further comprises means for directing a flow of gas across said illuminated surface area whereby said surface area can be dried.

19. The apparatus of claim 4 wherein said optical viewing means comprises a closed circuit video system comprising a video camera, optical coupling means therefore, and a video monitor whereby said focused image on said illuminated surface area can be enlarged and remotely displayed.

20. The apparatus of claim 19 wherein said scanning means comprises means for positioning said scan line with respect to said focused image so that it will extend across any selected portion of said focused image.

21. The apparatus of claim 20 further comprising a hand-held optical probe which comprises at least in part said means for illuminating said surface area with a focused image, and said optical viewing means for viewing said focused image.

22. The apparatus of claim 21 wherein said probe comprises means for providing an angle of incidence of about forty-five degrees, and for providing said optical viewing means having a line-of-sight which is substantially normal to said surface area.

23. The apparatus of claim 21 further comprising means for computing an inferred degree of anomalous subsurface structure in said article, and output means for identifying said inferred degree of anomalous subsurface structure to an operator of said apparatus.

24. The apparatus of claim 23 wherein said incident angle is about forty-five degrees, and said optical viewing means has a line-of-sight which is substantially normal to said illuminated surface area.

25. The apparatus of claim 24 wherein said probe further comprises a member of resilient material attached to the nose of said probe and so configured that said member comprises means for obviating ambient light from said illuminated surface area, and means for enabling positioning said probe with respect to the surface area of interest of said article so that the image plane of said incident beam is coincident with said surface.

26. The apparatus of claim 24 wherein said probe further comprises means for directing a flow of gas across said illuminated surface area whereby said surface area can be dried.

27. The apparatus of claim 26 wherein said probe further comprises a member of resilient material attached to the nose of said probe and so configured that said member comprises means for obviating ambient light from said illuminated surface area, and in which member said means for directing said flow of gas across said illuminated surface area comprises interconnected passageways and ports.

28. An optical probe for use in an optical instrumentation system comprising a remote light source, a flexible fiber optic cable for transmitting light from said source to said probe, a closed circuit video sub-system, and a flexible coherent fiber optic cable for conducting an image from said probe to said closed circuit video sub-system, said probe comprising means for being coupled to said fiber optic cables, means for projecting an image-carrying incident light beam from said probe and for focusing said beam to form said image on a solid surface of interest, and means for focusing light received from the direction of said surface of interest on the end of the flexible coherent fiber optic cable coupled to said probe whereby said video sub-system can view said surface of interest, and enlarge and remotely display a video image of said view of said surface of interest, said optical probe further comprising means for substantially obviating every portion of said incident light that is reflected from said surface from being transmitted to said video sub-system.

29. The optical probe of claim 28 wherein said means for obviating surface reflected light comprises an optical filter for circularly polarizing light which filter is so disposed that said incident light passes through it and so that any of said surface reflected incident light directed towards said means for focusing impinges on said filter whereby said surface reflected light is blocked from said video sub-system.

30. An optical probe for use in an optical instrumentation system comprising a remote light source, a flexible fiber optic cable for transmitting light from said source to said probe, a closed circuit video sub-system, and a flexible coherent fiber optic cable for conducting an image from said probe to said closed circuit video sub-system, said probe comprising means for being coupled to said fiber optic cables, means for projecting an image-carrying incident light beam from said probe and for focusing said beam to form said image on a solid surface of interest, and means for focusing light received from the direction of said surface of interest on the end of the flexible coherent fiber optic cable coupled to said probe whereby said video sub-system can view said surface of interest, and enlarge and remotely display a video image of said view of said surface of interest, said means for focusing said incident light beam comprising means for providing a fixed focal length for said beam so that said image is focused in an image plane, and means for spacing said probe so that said surface of interest is substantially coincident with said image plane, and said means for spacing comprises a resilient member disposed on the projection end of said probe which member has a length greater than the distance between the projection end of the probe and said image plane whereby said projection end of said probe can be pressed against said surface of interest to sufficiently deform said resilient member to cause said surface of interest and said image plane to be substantially coextensive.

31. The optical probe of claim 30 wherein said resilient member comprises means for obviating ambient light from said surface of interest, and means for conducting a flow of gas across said surface of interest.

* * * * *